US006083903A

United States Patent [19]
Adams et al.

[11] Patent Number: 6,083,903
[45] Date of Patent: *Jul. 4, 2000

[54] BORONIC ESTER AND ACID COMPOUNDS, SYNTHESIS AND USES

[75] Inventors: Julian Adams, Brookline; Yu-Ting Ma, Cambridge; Ross Stein, Sudbury; Matthew Baevsky, Cambridge; Louis Grenier, Cambridge; Louis Plamondon, Cambridge, all of Mass.

[73] Assignee: LeukoSite, Inc., Cambridge, Mass.

[ * ] Notice: This patent is subject to a terminal disclaimer.

[21] Appl. No.: 08/442,581

[22] Filed: May 16, 1995

Related U.S. Application Data

[63] Continuation-in-part of application No. 08/330,525, Oct. 28, 1994, abandoned.
[51] Int. Cl.[7] ..................................................... A61K 31/69
[52] U.S. Cl. .................................. 514/2; 514/64; 544/69; 546/13; 548/110; 548/405; 549/4; 549/213
[58] Field of Search ..................................... 548/110, 405; 544/69; 546/13; 549/4, 213; 514/2, 64

[56] References Cited

U.S. PATENT DOCUMENTS

| | | | |
|---|---|---|---|
| 5,106,948 | 4/1992 | Kinder et al. | 530/331 |
| 5,187,157 | 2/1993 | Kettner et al. | 514/18 |
| 5,242,904 | 9/1993 | Kettner et al. | 514/18 |
| 5,250,720 | 10/1993 | Kettner et al. | 558/288 |

FOREIGN PATENT DOCUMENTS

| | | |
|---|---|---|
| 93/01828 | 2/1993 | WIPO . |
| WO 94/21668 | 9/1994 | WIPO . |
| WO 95/09858 | 4/1995 | WIPO . |

*Primary Examiner*—Johann Richter
*Assistant Examiner*—John F. Dolan
*Attorney, Agent, or Firm*—Hale and Dorr LLP

[57] ABSTRACT

Disclosed herein are boronic ester and acid compounds, their synthesis and uses. More specifically, disclosed herein is a method for reducing the rate of degradation of proteins in an animal comprising contacting cells of the animal with certain boronic ester and acid compounds.

42 Claims, 3 Drawing Sheets

BORONIC ESTER AND ACID COMPOUNDS, SYNTHESIS AND USES

CROSS-REFERENCE TO RELATED APPLICATIONS

This application is a continuation-in-part of U.S. application Ser. No. 08/330,525, filed Oct. 28, 1994, now abandoned, the contents of which are incorporated herein by reference.

BACKGROUND OF THE INVENTION

1. Field of the Invention

The present invention relates to boronic ester and acid compounds, their synthesis and uses.

2. Description of Related Art

The synthesis of N-terminal peptidyl boronic ester and acid compounds, in general and of specific compounds, has been described previously (Shenvi et al. U.S. Pat. No. 4,499,082 issued Feb. 12, 1985; Shenvi et al. U.S. Pat. No. 4,537,773 issued Aug. 27, 1985; Siman et al. WO 91/13904 published Sep. 19, 1991; Kettner et al., *J. Biol. Chem.* 259(24):15106–15114 (1984)). These compounds have been shown to be inhibitors of certain proteolytic enzymes (Shenvi et al. U.S. Pat. No. 4,499,082 issued Feb. 12, 1985; Shenvi et al. U.S. Pat. No. 4,537,773; Siman et al. WO 91/13904 published Sep. 19, 1991; Kettner et al., *J. Biol. Chem.* 259(24):15106–15114 (1984)).

In the cytosol, there is a soluble proteolytic pathway that requires ATP and involves covalent conjugation of the cellular proteins with the small polypeptide ubiquitin ("Ub") (Hershko et al., *A. Rev. Biochem.* 61:761–807 (1992); Rechsteiner et al., *A. Rev. Cell. Biol.* 3:1–30 (1987)). Thereafter, the conjugated proteins are hydrolyzed by a 26S proteolytic complex containing a 20S degradative particle called the proteasome (Goldberg, *Eur. J. Biochem.* 203:9–23 (1992); Goldberg et al., *Nature* 357:375–379 (1992)). This multicomponent system is known to catalyze the selective degradation of highly abnormal proteins and short-lived regulatory proteins.

The 20S proteasome is composed of about 15 distinct 20–30 kDa subunits. It contains three different peptidase activities that cleave specifically on the carboxyl side of the hydrophobic, basic, and acidic amino acids (Goldberg et al., *Nature* 357:375–379 (1992); Goldberg, *Eur. J. Biochem.* 203:9–23 (1992); Orlowski, *Biochemistry* 29:10289 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992)). These peptidase activities are referred to as the chymotrypsin-like activity, the trypsin-like activity, and the peptidylglutamyl hydrolyzing activity, respectively.

Various inhibitors of the peptidase activities of the proteasome have been reported (Dick et al., *Biochemistry* 30:2725–2734 (1991); Goldberg et al., *Nature* 357:375–379 (1992); Goldberg, *Eur. J. Biochem.* 203:9–23 (1992); Orlowski, *Biochemistry* 29:10289 (1990); Rivett et al., *Archs. Biochem. Biophys.* 218:1 (1989); Rivett et al., *J. Biol. Chem.* 264:12,215–12,219 (1989); Tanaka et al., *New Biol.* 4:1–11 (1992); Murakami et al., *Proc. Natl. Acad. Sci. U.S.A.* 83:7588–7592 (1986); Li et al., *Biochemistry* 30:9709–9715 (1991); Goldberg, *Eur. J. Biochem.* 203:9–23 (1992); Aoyagi et al., *Proteases and Biological Control*, Cold Spring Harbor Laboratory Press (1975), pp. 429–454.

Stein et al., U.S. patent application Ser. No. 08/212,909 filed Mar. 15, 1994, describe the use of peptide aldehydes to 1) reduce the rate of loss of muscle mass in an animal by contacting cells of the muscle with a peptide aldehyde proteasome inhibitor, 2) reduce the rate of intracellular protein breakdown in an animal by contacting cells of the animal with a peptide aldehyde proteasome inhibitor, and 3) reduce the rate of degradation of p53 protein in an animal by administering to the animal a peptide aldehyde proteasome inhibitor.

Palombella et al., U.S. patent application Ser. No. 08/210,381 filed Mar. 18, 1994, describe the use of peptide aldehydes to reduce the cellular content and activity of NF-κB in an animal by contacting cells of the animal with peptide aldehyde inhibitor of proteasome function or ubiquitin conjugation.

The transcription factor NF-κB and other members of the rel family of protein complexes play a central role in the regulation of a remarkably diverse set of genes involved in the immune and inflammatory responses (Grilli et al., *International Review of Cytology* 143:1–62 (1993)). NF-κB exists in an inactive form in the cytosol complexed with an inhibitor protein, IκB. In order for the NF-κB to become active and perform its function, it must enter the cell nucleus. It cannot do this, however, until the IκB portion of the complex is removed, a process referred to by those skilled in the art as the activation of, or processing of, NF-κB. In some diseases, the normal performance of its function by the NF-κB can be detrimental to the health of the patient. For example, NF-κB is essential for the expression of the human immunodeficiency virus (HIV). Accordingly, a process that would prevent the activation of the NF-κB in patients suffering from such diseases could be therapeutically beneficial.

Goldberg and Rock, WO 94/17816, filed Jan. 27, 1994, describe the use of proteasome inhibitors to inhibit MHC-I antigen presentation. The ubiquitination/proteolysis pathway is shown to be involved in the processing of internalized cellular or viral antigens into antigenic peptides that bind to MHC-I molecules on an antigen presenting cell. Accordingly, inhibitors of this pathway would be useful for the treatment of diseases that result from undesired response to antigen presentation, including autoimmune diseases and transplant rejection.

Cyclins are proteins that are involved in cell cycle control in eukaryotes. Cyclins presumably act by regulating the activity of protein kinases, and their programmed degradation at specific stages of the cell cycle is required for the transition from one stage to the next. Experiments utilizing modified ubiquitin (Glotzer et al., *Nature* 349:132–138 (1991); Hershko et al., *J. Biol. Chem.* 266:376 (1991)) have established that the ubiquitination/ proteolysis pathway is involved in cyclin degradation. Accordingly, compounds that inhibit this pathway would cause cell cycle arrest and would be useful in the treatment of cancer, psoriasis, restenosis, and other cell proliferative diseases.

The present invention provides previously unsynthesized peptidyl boronic acid ester and acid compounds as well as methods for the use of peptidyl boronic ester and acid compounds, in general.

SUMMARY OF THE INVENTION

The present invention provides novel peptidyl boronic ester and acid compounds which are useful as proteasome inhibitors.

The present invention also provides a method for reducing the rate of intracellular protein breakdown. In a preferred embodiment, the present invention provides a method of inhibiting (reducing or preventing) the accelerated breakdown of muscle proteins that accompanies various physiological and pathological states and is responsible to a large extent for the loss of muscle mass (atrophy) that follows nerve injury, fasting, fever, acidosis, and certain endocrinopathies.

More particularly, the present invention provides a method for reducing the rate of muscle protein degradation in a cell comprising contacting said cell with a proteasome inhibitor of the structure (1) or (2) as follows:

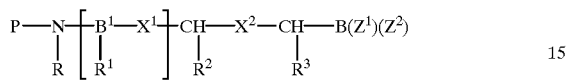
(1)

where
P is H or an amino-group-protecting moiety;
$B^1$ is independently selected from the group consisting of

and

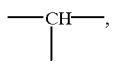

wherein if $B^1$ is

then $X^1$ is

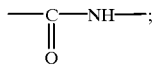

$X^1$ at each occurrence and $X^2$ are independently selected from the group consisting of

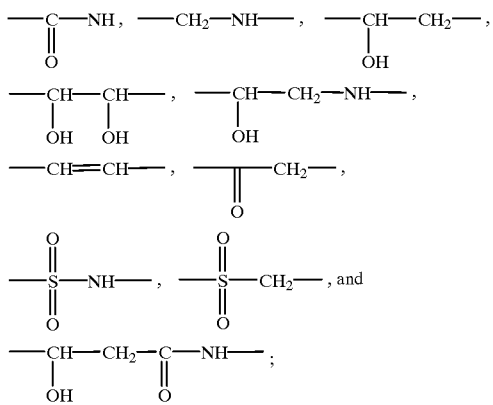

R is hydrogen or alkyl; or R together with the adjacent $R^1$ or $R^2$, if A=0, forms a nitrogen-containing heterocyclic ring;

$R^1$ at each occurrence, $R^2$, and $R^3$ are independently selected from the group consisting of hydrogen, alkyl, cycloalkyl, aryl, heterocycle and —$CH_2$—$R^5$,
where $R^5$ is aryl, aralkyl, alkaryl, cycloalkyl, heterocycle, or -chalcogen-alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0, 1, or 2 or

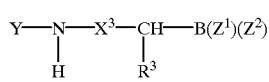
(2)

where
Y is

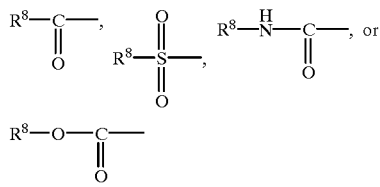

and $R^8$ is alkyl, aryl, alkaryl, aralkyl, or if Y is

or

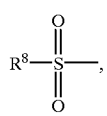

heterocycle;
$X^3$ is a covalent bond or

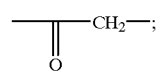

$R^3$ is selected from the group consisting of hydrogen, alkyl, cycloalkyl, aryl, heterocycle and —$CH_2$—$R^5$,
where $R^5$ is aryl, aralkyl, alkaryl, cycloalkyl, heterocycle, or -chalcogen-alkyl; and $Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O.

The present invention also provides a method for reducing the cellular content and activity of NF-κB in a cell comprising contacting the cell with a proteasome inhibitor of the structure (1) or (2) above. The inhibitors employed in the practice of the present invention are capable of preventing this activation. Thus, blocking NF-κB activity or production could have important application in various areas of medicine, e.g., inflammation, sepsis, AIDS, and the like.

The present invention also provides a method for reducing the rate of intracellular protein breakdown comprising contacting cells with a proteasome inhibitor of the structure (1) or (2) above.

The present invention further provides a method of reducing the rate of degradation of p53 protein in a cell comprising administering to the cell a proteasome inhibitor of the structure (1) or (2) above.

The present invention further provides a method for inhibiting cyclin degradation in a cell comprising contacting said cells with a proteasome inhibitor of the structure (1) or (2) above.

The present invention also provides a method for inhibiting antigen presentation in a cell comprising administering to the cell a proteasome inhibitor of the structure (1) or (2) above.

The present invention further provides a method for inhibiting cell adhesion in an animal comprising administering to said animal a proteasome inhibitor of the structure (1) or (2) above.

The present invention also provides a method for inhibiting HIV infection in an animal comprising administering to said animal a proteasome inhibitor of the structure (1) or (2) above.

The present invention also provides a method for treating cancer, psoriasis, restenosis, or other cell proliferative diseases in a patient comprising administering to said patient a proteasome inhibitor of the structure (1) or (2) above.

Inhibitors, such as those disclosed herein, provide an approach for inhibiting cytolytic immune responses. The proteasome inhibitors of structure (1) or (2) can be used to inhibit the processing of internalized cellular or viral antigens into antigenic peptides that bind to MHC-I molecules in an animal. The methods and drugs of this approach are useful for treating autoimmune diseases and preventing rejection of foreign tissues, such as transplanted organs or grafts.

Specifically, the inhibitors described herein inhibit the processing of internalized cellular or viral antigens into the kind of peptides, referred to as antigenic peptides, that bind to the MHC-I molecules. MHC-I binding peptides have strict sequence and size requirements. In the absence of the antigenic peptides, the antigens are not presented at the cell surface and $CD8^+$ T cells are not stimulated. Thus, the inhibitors of the present invention can block both the initiation of immune response and stop ongoing immune responses.

DESCRIPTION OF THE PREFERRED EMBODIMENTS

Figure 1:
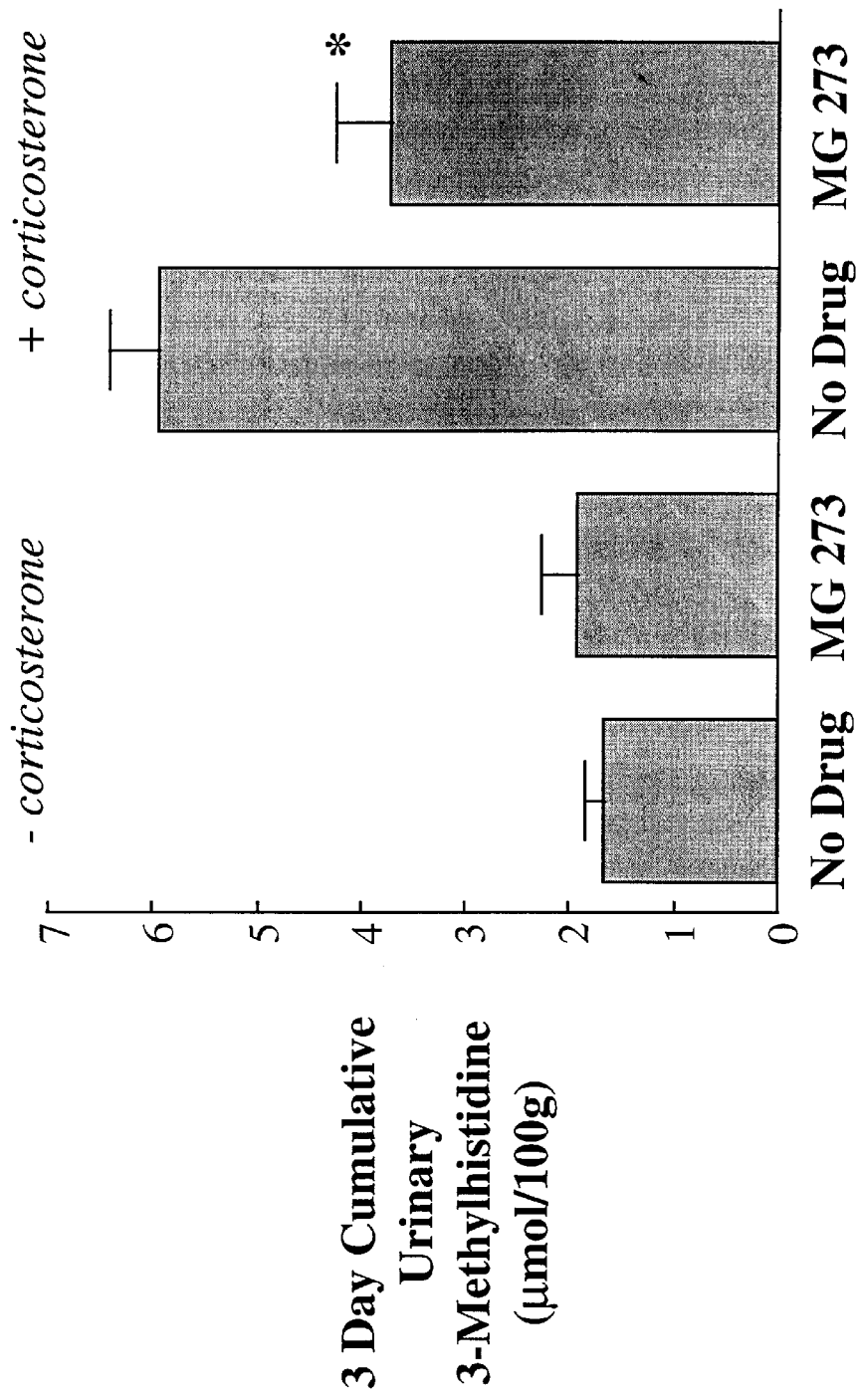
FIG. 1. Three day cumulative urinary 3-methylhistidine.

The present invention relates to proteasome inhibitors of the structure (1):

$$P-N(R)-[B^1(R^1)-X^1]_A-CH(R^2)-X^2-CH(R^3)-B(Z^1)(Z^2) \quad (1)$$

where

P is H or an amino-group-protecting moiety;

$B^1$ is independently selected from the group consisting of

—N(—)— and

—CH(—)—, wherein if $B^1$ is

—N(—)— then $X^1$ is

—C(=O)—NH—;

$X^1$ at each occurrence and $X^2$ are independently selected from the group consisting of

—C(=O)—NH—, —CH$_2$—NH—, —CH(OH)—CH$_2$—,

—CH(OH)—CH(OH)—, —CH(OH)—CH$_2$—NH—,

—CH=CH—, —C(=O)—CH$_2$—,

—S(=O)$_2$—NH—, —S(=O)$_2$—CH$_2$—, and

—CH(OH)—CH$_2$—C(=O)—NH—;

R is a hydrogen or alkyl; or together with the adjacent $R^1$, or $R^2$, if A=0, forms a nitrogen containing heterocyclic ring;

$R^1$ at every occurrence, $R^2$, and $R^3$ are independently selected from the group consisting of hydrogen, alkyl, cycloalkyl, aryl, heterocycle and —CH$_2$—$R^5$, where $R^5$ is aryl, aralkyl, alkaryl, cycloalkyl, heterocycle, or -chalcogen-alkyl, $Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0, 1, or 2.

The present invention also relates to proteasome inhibitors of the structure (2):

$$Y-\underset{H}{N}-X^3-\underset{R^3}{CH}-B(Z^1)(Z^2) \quad (2)$$

where

Y is $$R^8-\underset{O}{\overset{O}{C}}-, \quad R^8-\underset{O}{\overset{O}{\underset{\|}{S}}}-, \quad R^8-\underset{H}{N}-\underset{O}{\overset{O}{C}}-, \text{ or}$$

$$R^8-O-\underset{O}{\overset{}{C}}-$$

and $R^8$ is alkyl, aryl, alkaryl, aralkyl, or if Y is $$R^8-\underset{O}{\overset{}{C}}-$$

or $$R^8-\underset{O}{\overset{O}{\underset{\|}{S}}}-,$$

heterocycle;

$X^3$ is a covalent bond or $$-\underset{O}{\overset{}{C}}-CH_2-;$$

$R^3$ is selected from the group consisting of hydrogen, alkyl, cycloalkyl, aryl, heterocycle and —CH$_2$—R$^5$, where R$^5$ is aryl, aralkyl, alkaryl, cycloalkyl, heterocycle, or -chalcogen-alkyl; and $Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O.

In a preferred embodiment of the present invention, the P moiety of the proteasome inhibitor of structure (1) is:

$$R^7-\underset{O}{\overset{O}{C}}-, \quad R^7-\underset{O}{\overset{O}{\underset{\|}{S}}}-, \quad R^7-\underset{H}{N}-\underset{O}{\overset{O}{C}}-, \text{ or}$$

$$R^7-O-\underset{O}{\overset{}{C}}-$$

and $R^7$ is alkyl, aryl, alkaryl, aralkyl, or if Y is $$R^7-\underset{O}{\overset{}{C}}-$$

or $$R^7-\underset{O}{\overset{O}{\underset{\|}{S}}}-,$$

heterocycle.

Where $R^7$ is alkyl, it is preferably alkyl of from 1 to 4 carbon atoms, e.g., methyl, ethyl, propyl, butyl, or isomers thereof. Additionally, where $R^7$ is alkaryl or aralkyl, the alkyl moiety thereof is also preferably one having from 1 to 4 carbon atoms.

Where $R^7$ is aryl, it is preferably aryl of from 5 to 10 carbon atoms, wherein 1 or more of the carbon atoms can be replaced by O, N, or S, which may, if desired, be ring substituted. Additionally, where $R^7$ is alkaryl or aralkyl, the aryl moiety thereof is also preferably one having from 5 to 10 carbon atoms, wherein 1 or more of the carbons can be replaced by O, N or S.

It is preferred that $R^7$ be selected from the group consisting of:

$$H_3C-, \quad \text{(8-methylquinolinyl)}, \quad \text{(phenyl)}-CH_2-CH_2-,$$

$$H_3C-\text{(phenyl)}-, \quad \text{(2-methylquinolinyl)},$$

$$\text{(quinoxalinyl)}, \quad \text{(cyclohexyl)}, \quad \text{(3-methylpyridyl)},$$

$$\text{(pyrazinyl)}, \quad \text{(2-methylpyridyl)}, \quad \text{(phenyl)},$$

-continued

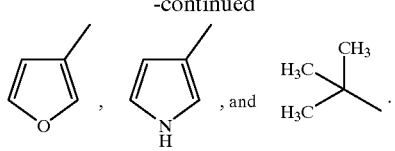

Most preferably, R⁷ is

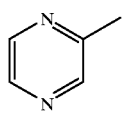

It is also preferred that P is

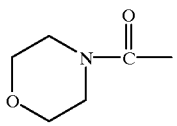

In a preferred embodiment of the present invention, the Y moiety of the proteasome inhibitor of structure (2) is:

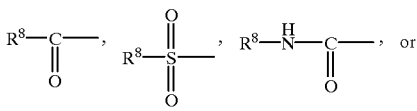

and R⁸ is alkyl, aryl, alkaryl, aralkyl, or if Y is

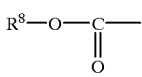

or

heterocycle.

Where R⁸ is alkyl, it is preferably alkyl of from 1 to 4 carbon atoms, e.g., methyl, ethyl, propyl, butyl, or isomers thereof. Additionally, where R⁸ is alkaryl or aralkyl, the alkyl moiety thereof is also preferably one having from 1 to 4 carbon atoms.

Where R⁸ is aryl, it is preferably aryl of from 6 to 10 carbon atoms, e.g., phenyl or naphthyl, which may, if desired, be ring substituted. Additionally, where R⁸ is alkaryl, aralkyl, aryloxy, alkaryloxy, or aralkoxy, the aryl moiety thereof is also preferably one having from 5 to 10 carbon atoms, wherein 1 or more of the carbons can be replaced by O, N or S. Preferably, the aryl moiety is a heterocycle (aromatic or saturated), more preferably an isomeric pyridine ring or morpholine ring.

In a more preferred embodiment, the Y moiety of the proteasome inhibitor of structure (2) is an isosteric amino acid replacement of structure (3)

(3)

wherein P and R¹ are as defined for structure (1).

Most preferably, Y is selected from the group consisting of acyl,

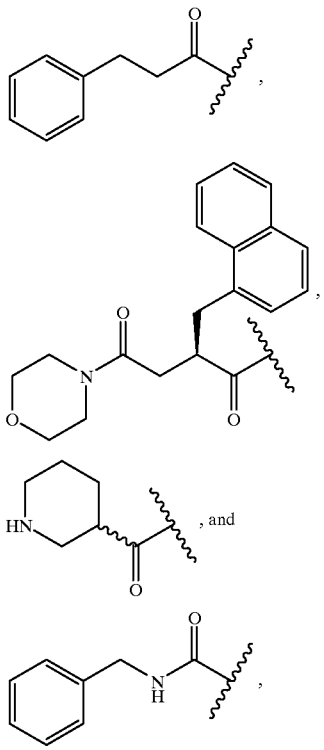

In structure (1), X represents a peptide bond or an isostere that can be used as a peptide bond replacement in the proteasome inhibitors to increase bioavailability and reduce hydrolytic metabolism. As noted above, X can be

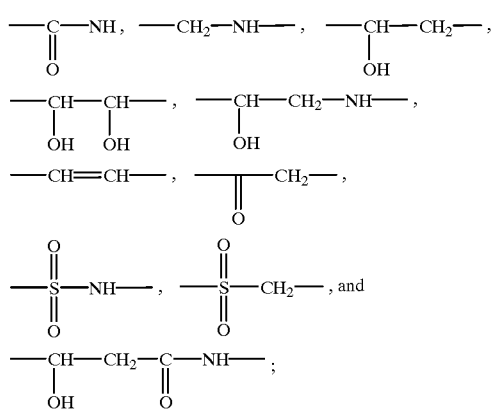

Preferably, X is

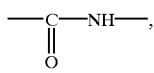

Introduction of these moieties into the proteasome inhibitors results in the following wherein $R_x$ and $R_y$ represent $R^1$, $R^2$, or $R^3$:

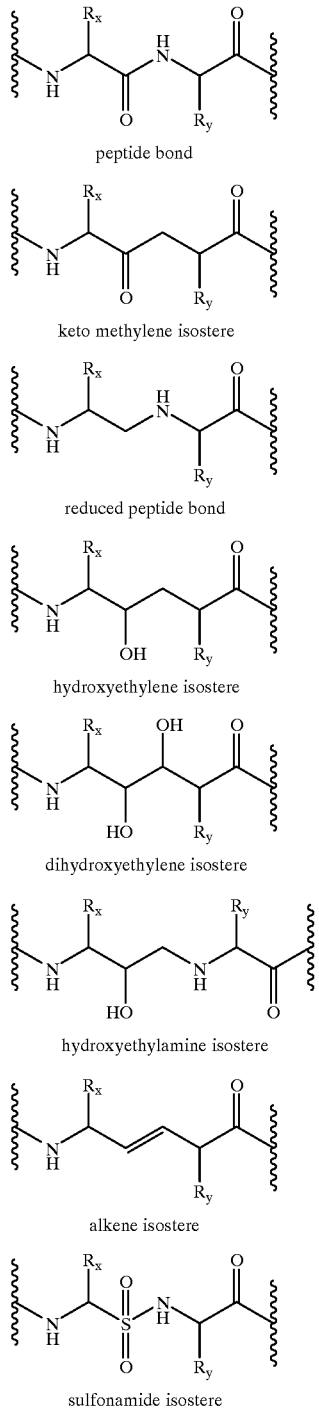

peptide bond keto methylene isostere reduced peptide bond hydroxyethylene isostere dihydroxyethylene isostere hydroxyethylamine isostere alkene isostere sulfonamide isostere -continued

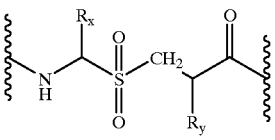

sulfone methylene isostester

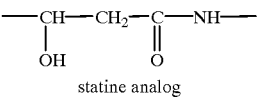

statine analog

For example, if Z-Leu-Leu-Leu-B(OH)$_2$ is found to undergo rapid hydrolytic metabolism to produce Z-Leu-OH and H$_2$N-Leu-Leu-B(OH)$_2$, the hydroxyethylene isostere can be prepared to eliminate this reaction:

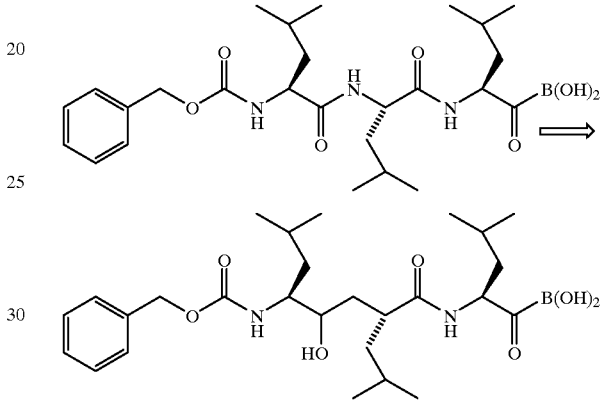

Another isostere within the scope of the present invention is the aza-peptide isostere. This is the result of the replacement of the α-carbon atom of an amino acid with a nitrogen atom, e.g.,

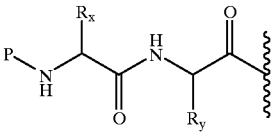

wherein $R_x$ represents $R^1$ and $R_y$ represents $R^2$.

As noted above, A in structure (1) can be either 0, 1 or 2. Thus, when A is 0, the amino acid residue within the brackets is not present and the inhibitor is a dipeptide. Similarly, where A is 1, the amino acid residue within the brackets is present and the inhibitor is a tripeptide. It is preferred that A be 0.

It is preferred that $R^1$, $R^2$, and $R^3$ in structure (1) be independently selected from the group consisting of alkyl and —CH$_2$—R$^5$. More preferably, $R^1$, $R^2$ and $R^3$ are independently selected from the group consisting of alkyl groups of from 1 to 4 carbon atoms, e.g., methyl, ethyl, propyl, butyl, or isomers thereof, e.g., isopropyl, isobutyl, sec-butyl, t-butyl, or —CH$_2$—R$^5$, where $R^5$ is cycloalkyl, aryl, or heterocycle. It is more preferred that at least one of $R^1$ and $R^2$ be isobutyl or CH$_2$—R$^5$, and most preferred that $R^2$ is CH$_2$—R$^5$.

It is preferred that $R^5$ is aryl of 5 to 10 carbon atoms, wherein 1 or more carbons may be replaced by oxygen, nitrogen or sulfur.

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl,2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, phenanthrolinyl, phenazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and Spiro compounds containing, for example, the above heterocycles.

The term "substituted", as used herein, means that one or more hydrogens of the designated moiety is replaced with a selection from the indicated group, provided that no atom's normal valency is exceeded, and that the substitution results in a stable compound. When a substituent is keto (i.e., =O), then 2 hydrogens attached to an atom of the moiety are replaced.

By "stable compound" or "stable structure" is meant herein a compound that is sufficiently robust to survive isolation to a useful degree of purity from a reaction mixture and formulation into an efficacious therapeutic agent.

Most preferably, $R^2$ is

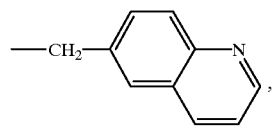

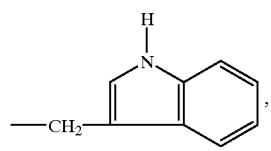

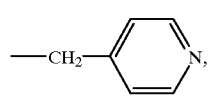

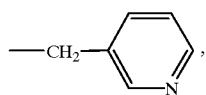

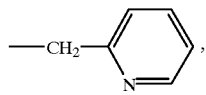

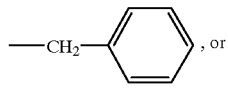, or

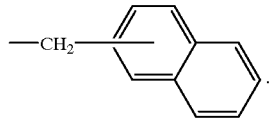.

Where $R^1$, $R^2$ or $R^3$ is a substituted alkyl, it is preferably an alkyl of from 1 to 4 carbon atoms substituted with at least one aryl group of from 6 to 10 carbon atoms or at least one cycloalkyl group, preferably a cycloalkyl group having 5 or 6 carbon atoms, which groups may be substituted or unsubstituted.

Where $R^1$, $R^2$, $R^3$, or $R^5$ is substituted aryl, it is preferably substituted with at least one alkyl group of from 1 to 4 carbon atoms, which groups may be substituted or unsubstituted.

Where $R^1$, $R^2$, $R^3$ or $R^5$ is cycloalkyl, it is preferably cycloalkyl of from 5 to 6 carbon atoms, e.g., cyclopentyl or cyclohexyl, which groups may be substituted or unsubstituted.

Where $R^1$, $R^2$, $R^3$ or $R^5$ is substituted cycloalkyl, it is preferably substituted with at least one aryl group from 6 to 10 carbon atoms or at least one alkyl group, preferably an alkyl group having 1 to 4 carbon atoms, which groups may be substituted or unsubstituted.

Where $R^1$, $R^2$ or $R^3$ is —Y—$R^6$, Y is a chalcogen, preferably oxygen or sulfur, more preferably sulfur; and $R^6$ is alkyl, preferably alkyl of from 1 to 4 carbon atoms, e.g., methyl, ethyl, propyl, butyl, or isomers thereof.

R in the structure shown above is hydrogen or alkyl, or R together with the adjacent $R^1$, or $R^2$ if A=0, forms a nitrogen-containing heterocyclic ring. It is preferred that the heterocyclic ring be chosen from the group consisting of

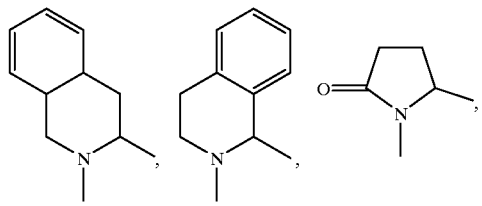

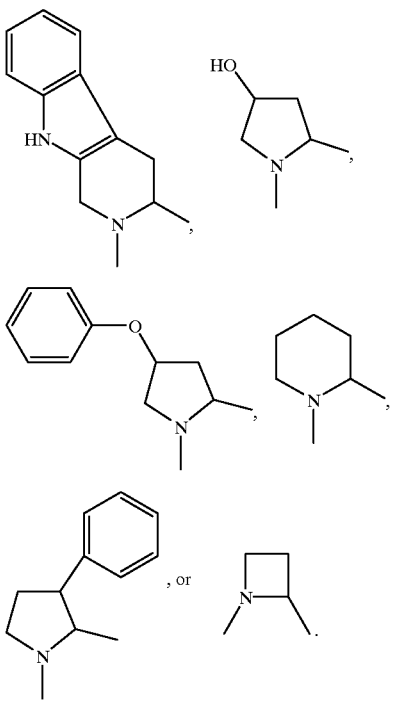

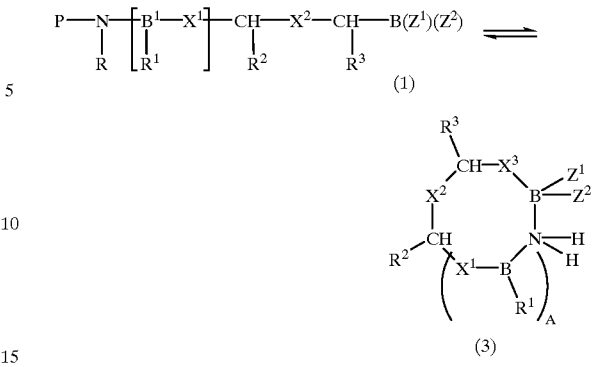

Where R is alkyl, it is preferably alkyl of from 1 to 4 carbon atoms, e.g., methyl, ethyl, propyl, butyl, or isomers thereof.

It is preferred that $Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms and, optionally, a heteroatom or heteroatoms which can be N, S, or O. When $Z^1$ or $Z^2$ together form a dihydroxy compound, it is preferred that the dihydroxy compound be pinacol, perfluoropinacol, pinanediol, ethylene glycol, diethylene glycol, 1,2-cyclohexanediol, 1,3-propopanediol, 2,3-butanediol, glycerol, diethanolamine or other amino alcohols, or other equivalents apparent to those skilled in the art. When $Z^1$ or $Z^2$ is alkyl or alkoxy, the alkyl group preferably has 1 to 4 carbon atoms. Most preferably $Z^1$ and $Z^2$ are hydroxy.

Examples of suitable proteasome inhibitors include without limitation, the following compounds:

N-(4-Morpholine)carbonyl-β-(1-naphthyl)-L-alanine-L-leucine boronic acid,

N-(8-quinoline)sulfonyl-β-(1-naphthyl)-L-alanine-L-leucine boronic acid,

N-(2-pyrazine)carbonyl-L-phenylalanine-L-leucine boronic acid,

L-proline-L-leucine boronic acid,

N-(2-quinoline)carbonyl-L-homophenylalanine-L-leucine boronic acid,

N-(3-Pyridine)carbonyl-L-phenylalanine-L-leucine boronic acid,

N-(3-phenylpropionyl)-L-phenylalanine-L-leucine boronic acid, and

N-(4-Morpholine)carbonyl-L-phenylalanine-L-leucine boronic acid.

When P and R are both H, structure (1) will exist in equilibrium with a cyclic structure (3), which is considered to be covered by the current invention:

The above-described boronic ester and acid compounds include both D and L peptidyl configurations. However, L configurations are preferred.

The present invention relates to a method for reducing the rate of muscle protein degradation in a cell comprising contacting the cell with a proteasome inhibitor described above. More specifically, the present invention relates to a method for reducing the rate of loss of muscle mass in an animal comprising contacting cells of the muscle with a proteasome inhibitor described above.

The present invention also relates to a method for reducing the cellular content and activity of NF-κB in a cell comprising contacting the cell with a proteasome inhibitor described above. More specifically, the present invention also relates to a method for reducing the cellular content and activity of NF-κB in an animal comprising contacting cells of the animal with a proteasome inhibitor described above.

The present invention also relates to a method for reducing the rate of intracellular protein breakdown comprising contacting cells with a proteasome inhibitor described above. More specifically, the present invention also relates to a method for reducing the rate of intracellular protein breakdown in an animal comprising contacting cells of the animal with the proteasome inhibitor described above.

The present invention further relates to a method of reducing the rate of degradation of p53 protein in a cell comprising administering to the cell a proteasome inhibitor described above. More specifically, the present invention further provides a method of reducing the rate of degradation of p53 protein in an animal (preferably, an animal subjected to DNA damaging drugs or radiation) comprising administering to said animal a proteasome inhibitor described above.

The present invention further relates to a method for inhibiting cyclin degradation in a cell comprising contacting said cells with a proteasome inhibitor described above. More specifically, the present invention relates to a method for inhibiting cyclin degradation in an animal comprising contacting cells of said animal with a proteasome inhibitor described above.

The present invention also relates to a method for inhibiting antigen presentation in a cell comprising administering to the cell a proteasome inhibitor described above. More specifically, the present invention relates to a method for inhibiting antigen presentation in animal comprising administering to the animal a proteasome inhibitor described above.

The present invention further provides a method for inhibiting cell adhesion in an animal comprising administering to said animal a proteasome inhibitor described above.

The present invention also provides a method for inhibiting HIV infection in an animal comprising administering to said animal a proteasome inhibitor described above.

The present invention also provides a method for treating cancer, psoriasis, restenosis, or other cell proliferative diseases in a patient comprising administering to the patient a proteasome inhibitor described above.

The "animals" referred to herein are preferably mammals. Both terms are intended to include humans.

Preferably, the methods described above deliver the proteosome inhibitor by either contacting cells of the animal with a proteasome inhibitor described above or by administering to the animal a proteasome inhibitor described above.

The present invention relates to a method of inhibiting (reducing or preventing) the accelerated or enhanced proteolysis that occurs in atrophying muscles and is known to be due to activation of a nonlysosomal ATP-requiring process in which ubiquitin plays a critical role.

Inhibition of the ATP-ubiquitin-dependent pathway is a new approach for treating the negative nitrogen balance in catabolic states. This can be effected through use of an inhibitor of the present invention, resulting in reduction of loss of muscle mass in conditions in which it occurs. Such an inhibitor can also be used in reducing the activity of the cytosolic ATP-ubiquitin-dependent proteolytic system in cell types other than muscle cells. Excessive protein loss is common in many types of patients, including individuals with sepsis, burns, trauma, many cancers, chronic or systemic infections, neuromotor degenerative disease, such as muscular dystrophy, acidosis, or spinal or nerve injuries. It also occurs in individuals receiving corticosteroids, and those in whom food intake is reduced and/or absorption is compromised. Moreover, inhibitors of the protein breakdown pathway could possibly be valuable in animals, e.g., for combatting "shipping fever", which often leads to a major weight loss in cattle or pigs.

The accelerated proteolysis evident in atrophy of skeletal muscles upon denervation or fasting is catalyzed by the nonlysosomal ATP-dependent degradative pathway. It has been shown that in a variety of catabolic states (e.g., denervation, fasting, fever, certain endocrinopathies or metabolic acidosis) muscle wasting is due primarily to accelerated protein breakdown and, in addition, that the increased proteolysis results from activation of the cytosolic ATP-ubiquitin-dependent proteolytic system, which previously had been believed to serve only in the rapid elimination of abnormal proteins and certain short-lived enzymes. The discovery that this pathway is responsible for the accelerated proteolysis in these catabolic states is based on studies in which different proteolytic pathways were blocked or measured selectively in incubated muscles, and the finding of increased mRNA for components of this pathway (e.g., for ubiquitin and proteasome subunits) and increased levels of ubiquitin-protein conjugates in the atrophying muscles. The nonlysosomal ATP-ubiquitin-dependent proteolytic process increases in muscle in these conditions and is responsible for most of the accelerated proteolysis that occurs in atrophying muscles. There is a specific increase in ubiquitin mRNA, induction of mRNA for proteasome and increased ubiquitinated protein content in atrophying muscles that is not seen in non-muscle tissue under the same conditions.

The inhibitors of the present invention can be used to reduce (totally or partially) the nonlysosomal ATP-dependent protein degradation shown to be responsible for most of the increased protein degradation that occurs during fasting, denervation, or disuse (inactivity), steroid therapy, febrile infection, and other conditions.

One approach to testing drug candidates for their ability to inhibit the ATP-ubiquitin-dependent degradative process is to measure proteolysis in cultured cells (Rock, et al., *Cell* 78:761 (1994)). For example, the degradation of long-lived intracellular proteins can be measured in mouse C2C12 myoblast cells. Cells are incubated with $^{35}$S-methionine for 48 hours to label long-lived proteins and then chased for 2 hours with medium containing unlabeled methionine. After the chase period, the cells are incubated for 4 hours in the presence or absence of the test compound. The amount of protein degradation in the cell can be measured by quantitating the trichloroacetic acid soluble radioactivity released from the prelabeled proteins into the growth medium (an indicator of intracellular proteolysis).

Inhibitors can also be tested for their ability to reduce muscle wasting in vivo. Urinary excretion of the modified amino acid 3-methyl histidine (3-MH) is probably the most well characterized method for studying myofibrillar protein degradation in vivo (see Young and Munro, *Federation Proc.* 37:229–2300 (1978)). 3-Methylhistidine is a post-translationally modified amino acid which cannot be reutilized for protein synthesis, and it is only known to occur in actin and myosin. It occurs in actin isolated from all sources, including cytoplasmic actin from many different cell types. It also occurs in the myosin heavy chain of fast-twitch (white, type II) muscle fibers, but it is absent from myosin of cardiac muscle and myosin of slow-twitch (red, type I) muscle fibers. Due to its presence in actin of other tissues than skeletal muscle, other tissues will contribute to urinary 3-MH. Skeletal muscle has been estimated to contribute 38–74% of the urinary 3-MH in normal rats and 79–86% of the urinary 3-MH in rats treated with corticosterone (100 mg/kg/day subcutaneously) for 2–4 days (Millward and Bates, *Biochem. J.* 214:607–615 (1983); Kayali, et al., *Am. J. Physiol.* 252:E621–E626 (1987)).

High-dose glucocorticoid treatment is used to induce a state of muscle wasting in rats. Treating rats with daily subcutaneous injections of corticosterone (100 mg/kg) causes an increase of approximately 2-fold in urinary 3-MH. The increase in excretion of 3-MH is transient, with a peak increase after 2–4 days of treatment and a return to basal values after 6–7 days of treatment (Odedra, et al., *Biochem. J.* 214:617–627 (1983); Kayali, et al., *Am. J. Physiol.* 252:E621–E626 (1987)). Glucocorticoids have been shown to activate the ATP-ubiquitin-dependent proteolytic pathway in skeletal muscle (Wing and Goldberg, *Am. J. Physiol.* 264:E668–E676 (1993)) and proteasome inhibitors are therefore expected to inhibit the muscle wasting that occurs after glucocorticoid treatment.

The inhibitors can be used in vitro or in vivo. They can be administered by any number of known routes, including orally, intravenously, intramuscularly, topically, and by infusion (Platt et al., U.S. Pat. No. 4,510,130; Badalamente et al., *Proc. Natl. Acad. Sci. U.S.A.* 86:5983–5987 (1989); Staubli et al., *Brain Research* 444:153–158 (1988)) and will generally be administered in combination with a physiologically acceptable carrier (e.g., physiological saline). The effective quantity of inhibitor given will be determined empirically and will be based on such considerations as the particular inhibitor used, the condition of the individual, and the size and weight of the individual. They can be administered alone or in combination with another inhibitor or an inhibitor of another pathway (e.g., a lysosomal or $Ca^{++}$-dependent pathway) responsible for loss of muscle mass.

Use of Proteasome Inhibitors as Agents that Selectively Protect Normal Cells from DNA Damage During Radiation and Chemotherapy Treatment of Tumors The inhibitors of the present invention will block the degradation of the tumor suppressor protein p53. This protein is degraded by the ATP ubiquitin dependent proteolysis by the proteasome (see Scheffner et al., *Cell*75:495–505 (1993)).

Studies of p53 knockout mice indicate an important role for p53 in reducing incidence of tumors (Donehower et al.,

*Nature* 356:215–221 (1992)). In normal cells expressing wild type, unmutated p53, the basal levels of p53 are very low due to very rapid degradation of p53 protein. However, expression of p53 protein in normal cells is stimulated in response to radiation and drugs that induce DNA damage (Kastan et al., *Cancer Res.* 51:6304–6311 (1991)). These induced high levels of wild type, unmutated p53 induce arrest of normal cell proliferation at the G1 stage of the cell cycle (Kastan et al., supra; Kuerbitz, *PNAS* 89:7491–7495 (1992)). This arrest of cell proliferation permits repair of damaged DNA. By contrast, in tumor cells expressing mutant forms of p53, DNA damaging drugs or radiation do not induce cell cycle arrest (Kastan et al., supra; Kastan et al., *Cell* 71:587–597 (1992)). Consequently, tumor cells are selectively damaged by radiation and cytotoxic drugs.

The selective arrest response of normal cells by inducing p53 suggests that enhancing the p53 response may allow the treatment of the tumor with higher/more prolonged tumoricidal doses of radiation or antineoplastic drugs. The idea that induction of p53 by a non toxic agent as an adjunct to radiotherapy has been reported previously (Lane, *Nature* 358:15–16 (1992), but a method for reducing it to practice was not described.

The use of proteasome inhibitors provides a method for augmenting the expression of p53 in normal cells by preventing its degradation by the proteasome. An example of this would be the systemic administration of proteasome inhibitor at a sufficient dose to inhibit p53 degradation by the proteasome during the treatment of the tumor with cytotoxic drugs or radiation. This will prolong and increase the levels of p53 expression in normal cells and will enhance the arrest of normal cell proliferation, reducing their sensitivity to higher doses of radiation or cytotoxic drugs. Administration of proteasome inhibitors would therefore permit exposing the tumor to higher doses of radiation, enhancing the killing of tumor cells. Thus, proteasome inhibitors can be used as adjuvants to therapy with tumoricidal agents, such as radiation and cytotoxic drugs.

Topical Application of Proteasome Inhibitors to Enhance p53 Expression in Skin

The expression of p53 in normal skin is induced by exposure of the skin to UV irradiation, which inhibits DNA replication that is needed for cell division (Maltzman et al., *Mol. Cell. Biol.* 4:1689 (1984); Hall et al., *Oncogene* 8:203–207 (1993)). This protects normal skin from chromosomal DNA damage by allowing time for DNA repair before DNA replication.

Defects in the p53 response pathway, such as seen with Ataxia Telangiectasia, result in increased susceptibility to ionizing radiation-induced skin tumors (Kastan et al., *Cell* 71:587–597 (1992)). It is well established that exposure of normal individuals increases the risk for many kinds of skin cancers. This risk can be diminished by UV filtering chemicals in skin creams. Another approach would be to promote the resistance of the DNA in skin cells to UV damage by the topical application of agents that enhance the skin's expression of p53 in response to UV light. Inhibiting p53 degradation by the topical application of proteasome inhibitors provides a method to enhance the p53 response.

One preferred embodiment of the present invention is the topical application of proteasome inhibitors to reduce the acknowledged risk of skin cancers that results from the treatment of psoriasis using UV light, which is often combined with psoralens or coal tar. Each of these agents can induce DNA damage.

Use of Proteasome Inhibitors to Reduce the Cellular Content and Activity of NF-κB NF-κB exists in an inactive form in the cytosol complexed with an inhibitor protein, IκB. In order for the NF-κB to become active and perform its function, it must enter the cell nucleus. It cannot do this, however, until the IκB portion of the complex is removed, a process referred to by those skilled in the art as the activation of, or processing of, NF-κB. In some diseases, the normal performance of its function by the NF-κB can be detrimental to the health of the patient. For example, as mentioned above, NF-κB is essential for the expression of the human immunodeficiency virus (HIV). Accordingly, a process that would prevent the activation of the NF-κB in patients suffering from such diseases could be therapeutically beneficial. The inhibitors employed in the practice of the present invention are capable of preventing this activation. Thus, blocking NF-κB activity or production could have important application in various areas of medicine, e.g., inflammation, through the inhibition of expression of inflammatory cytokines and cell adhesion molecules, (ref. Grilli et al., *International Review of Cytology* 143: 1–62 (1993)) sepsis, AIDS, and the like.

More specifically, the activity of NF-κB is highly regulated (Grilli et al., *International Review of Cytology* 143: 1–62 (1993); Beg et al., *Genes and Development* 7:2064–2070 (1993)). NF-κB comprises two subunits, p50 and an additional member of the rel gene family, e.g., p65 (also known as Rel A). In most cells, the p50 and p65 are present in an inactive precursor form in the cytoplasm, bound to IκB. In addition, the p50 subunit of NF-κB is generated by the proteolytic processing of a 105 kD precursor protein NF-κB$_1$ (p105), and this processing is also regulated. The sequence of the N-terminal 50 kD portion of p105 is similar to that of p65 and other members of the rel gene family (the rel homology domain). By contrast, the C-terminal 55 kD of p105 bears a striking resemblance to IκB-α (also known as MAD3). Significantly, unprocessed p105 can associate with p65 and other members of the rel family to form a p65/p105 heterodimer. Processing of p105 results in the production of p50, which can form the transcriptionally active p50/p65 heterodimer. The C-terminal IκB-α-homologous sequence of p105 is rapidly degraded upon processing.

There is another rel-related protein, NF-κB$_2$ (p100), that is similar to p105 in that it, too, is processed to a DNA binding subunit, p52 (Neri et al., *Cell* 67:1075 (1991); Schmid et al., *Nature* 352:733 (1991); Bours et al., *Molecular and Cellular Biology* 12:685 (1992); Mercurio et al., *DNA Cell Biology* 11:523 (1992)). Many of the structural and regulatory features of p100 are similar to p105. In addition, the p100 protein can also form a heterodimer with p65 and other rel family members.

In summary, the transcriptional activity of heterodimers consisting of p50 and one of the many rel family proteins, such as p65, can be regulated by at least two mechanisms. First, the heterodimers associate with IκB-α to form an inactive ternary cytoplasmic complex. Second, the rel family members associate with p105 and p100 to form inactive complexes. The ternary complex can be activated by the dissociation and destruction of IκB-α, while the p65/p105 and p65/p100 heterodimer can be activated by processing p105 and p100, respectively.

The dissociation of IκB-α can be induced by a remarkably large number of extracellular signals, such as lipopolysaccharides, phorbol esters, TNF-α, and a variety of cytokines. The IκB-α is then rapidly degraded. Recent studies suggest that p105 and p100 processing can also be induced by at least some of these extracellular signals.

Studies have demonstrated that p105 or a truncated form of p105 (p60Tth) can be processed to p50 in vitro (Fan et al., *Nature* 354:395–398 (1991)). Certain of the requirements and characteristics of this in vitro processing reaction (e.g., ATP/Mg$^{++}$ dependency) implicated the involvement of the ubiquitin-mediated protein degradation pathway (Goldberg, *Eur. J. Biochem.* 203:9–23 (1992), Hershko et al., *Annu. Rev. Biochem.* 61:761–807 (1992)).

The proteasome is required for the processing of p105 to p50. p105/p60Tth proteins are not processed in mammalian cell cytoplasmic extracts depleted of proteasome activity. However, addition of purified 26S proteasomes to these depleted extracts restores the processing activity. Additionally, specific inhibitors of the proteasome block the formation of p50 in mammalian cell extracts and in vivo. Also, mammalian p105 is processed to p50 in *Saccharomyces cerevisiae* in vivo, and a mutant in the chymotrypsin-like activity of the proteasome results in a significant decrease in p105 processing. p60Tth is ubiquitinated in vitro and this ubiquitination is a pre-requisite for p105 processing.

As mentioned above, the C-terminal half of the p105 (p105C') is rapidly degraded during the formation of p50 and the sequence of p105C' is remarkably similar to that of IκB. IκB-α is rapidly degraded in response to NF-κB inducers and this degradation has been shown to be necessary for the activation (Mellits et al., *Nucleic Acids Research* 21(22):5059–5066 (1993); Henkel et al., *Nature* 365: 182–185 (1993); Beg et al., *Molecular and Cellular Biology* 13(6):3301–3310 (1993)). IκB-α degradation and the activation of NF-κB is also blocked by inhibitors of proteasome function or ubiquitin conjugation (Palombella et al., *Cell* 78:773–785 (1994)).

Accordingly, the proteasome plays an essential role in the regulation of NF-κB activity. First, the proteasome is required for the processing of p105 and possibly p100. The degradation of the inhibitory C-terminus may also require the proteasome. Second, the proteasome appears to be required for the degradation of IκB-α in response to extracellular inducers.

The present invention preferably relates to the use of proteasome inhibitors of the above-described structures.

The present invention relates to a method for reducing the cellular content and activity of NF-κB in an animal comprising contacting cells of the animal with inhibitors of proteasome function.

Compounds can be tested for their ability to inhibit the activation of NF-κB by means of a DNA binding assay (Palombella, et al., *Cell* 78:773 (1994)). Whole-cell extracts are prepared from untreated or TNF-α treated cells that have been pretreated for 1 hour with the test compound. The DNA binding activity of NF-κB is measured by an electrophoretic mobility shift assay using the PRDII probe from the human IFN-β gene promoter.

As an indirect measure of NF-κB activation, the cell-surface expression of E-selectin, I-CAM-1, and V-CAM-1 on primary human umbilical vein endothelial cells (HUVECs) can be determined by means of a cell surface fluorescent immuno-binding assay. Because E-selectin, I-CAM-1, and V-CAM-1 are under the regulatory control of NF-κB, inhibition of NF-κB activation results in reduced levels of these adhesion molecules on the cell surface.

Compounds can also be tested for their ability to inhibit a delayed-type hypersensitivity response in mice. Contact hypersensitivity is a manifestation of an in vivo T-cell mediated immune response (Friedmann, Curr. *Opinion Immunology*, 1:690–693 (1989)). Although the exact molecular mechanisms that regulate the cellular interactions and vascular changes involved in the response remain obscure, it is clear that the process is dependent upon the interplay of soluble mediators, adhesion molecules, and the cytokine network (Piguet, et al., *J. Exp. Med.* 173:673–679 (1991); Nickoloff, et al. *J. Invest. Dermatol.* 94:151S–157S (1990)). NF-κB, by mediating events such as the production of cytokines and the induction and utilization of cell-surface adhesion molecules, is a central and coordinating regulator involved in immune responses.

The present invention will now be illustrated by the following examples, which are not intended to be limiting in any way.

EXAMPLES

Most compounds of structure (1) or (2) were prepared according to the general reaction sequence depicted in Scheme 1. The general procedures employed for each compound are summarized in Table I, and detailed descriptions of these procedures are provided in the Examples. Syntheses that do not conform to the general reaction sequence are described in full in the Examples. (1S,2S,3R,5S)-Pinanediol leucine boronate trifluoroacetate salt was prepared as reported (Kettner, C. A.; Shenvi, A. B. *J. Biol. Chem.* 259:15106 (1984)). N-Protected (Boc-, Cbz-, or Fmoc-) amino acids were commercially available or were prepared from the corresponding free amino acid by standard protection methods, unless otherwise described in the Examples. 1-Ethyl-3-(3-dimethylaminopropyl)carbodiimide hydrochloride (EDC), benzotriazol-1-yloxytris(dimethylamino) phosphonium hexafluorophosphate (BOP reagent), or O-(1H-benzotriazol-1-yl)-N,N,N',N'-tetramethyluronium tetrafluoroborate (TBTU) were employed as coupling reagents (Sheehan, J. C. et al., *J. Am. Chem. Soc.* 87:2492 (1965); Castro, B., et al., *Synthesis* 11:751 (1976); *Tetrahedron Lett.* 30:1927 (1989)). All compounds were characterized by proton nuclear magnetic resonance (NMR) spectroscopy. The purity of the products was verified by thin layer chromatography and by high performance liquid chromatography (HPLC).

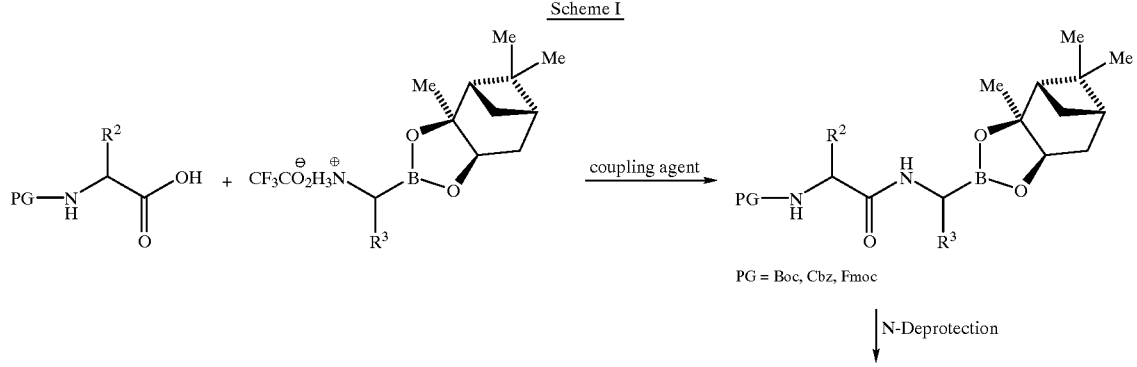

Scheme I

PG = Boc, Cbz, Fmoc

N-Deprotection

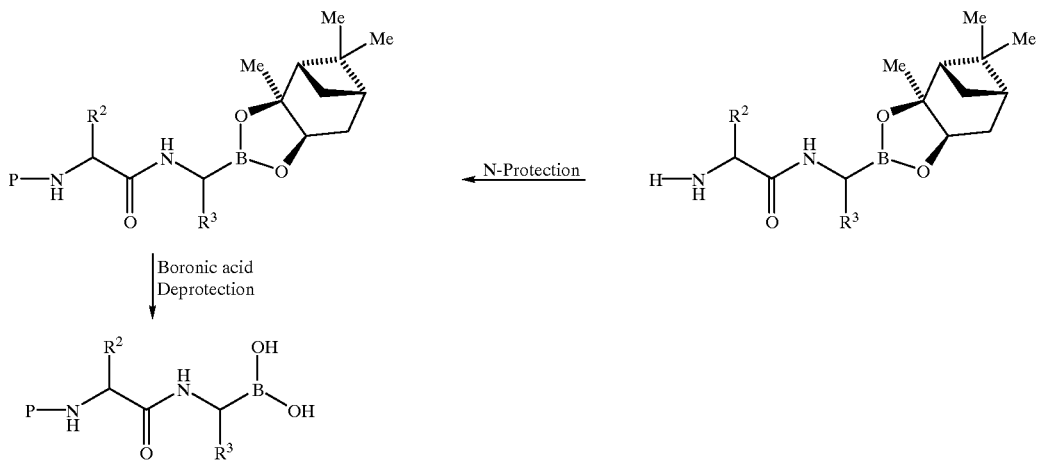

TABLE I

Synthesis of Boronic Ester and Acid Compounds

| Compound | Coupling Agent | Boronic Acid Deprotection[a] | N-Terminal Protection |
|---|---|---|---|
| MG-261 | EDC | — | — |
| MG-262 | EDC | A | — |
| MG-264 | BOP | — | — |
| MG-267 | EDC | — | — |
| MG-268 | EDC | A | NaH, MeI |
| MG-270 | EDC | A | — |
| MG-272 | EDC | A | — |
| MG-273 | EDC | A, B | RC(O)Cl |
| MG-274 | BOP | A | — |
| MG-278 | EDC | A | RC(O)Cl |
| MG-282 | EDC | A | — |
| MG-283 | BOP | A | $Ac_2O$ |
| MG-284 | — | B | RC(O)Cl |
| MG-285 | BOP | A | RC(O)Cl |
| MG-286 | EDC | A, B | RC(O)Cl |
| MG-287 | EDC | B | $Ac_2O$ |
| MG-288 | EDC | A | RC(O)Cl |
| MG-289 | EDC | B | $RS(O)_2Cl$ |
| MG-290 | EDC | B | $Ac_2O$ |
| MG-291 | EDC | B | $RS(O)_2Cl$ |
| MG-292 | BOP | B | RC(O)Cl |
| MG-293 | TBTU | B | RC(O)Cl |
| MG-294 | EDC | B | — |
| MG-295 | BOP | B | $RS(O)_2Cl$ |
| MG-296 | EDC | B | $RS(O)_2Cl$ |
| MG-297 | EDC | B | $RS(O)_2Cl$ |
| MG-298 | EDC | B | RC(O)Cl |
| MG-299 | EDC | B | RC(O)Cl |
| MG-300 | EDC | B | RC(O)Cl |
| MG-301 | BOP | B | $Ac_2O$ |
| MG-302 | EDC | B | — |
| MG-303 | EDC | B | HCl, ether |
| MG-304 | TBTU | B | — |
| MG-305 | EDC | B | RC(O)Cl |
| MG-306 | TBTU | B | RC(O)Cl |
| MG-307 | TBTU | B | RC(O)Cl |
| MG-308 | TBTU | B | RC(O)Cl |
| MG-309 | TBTU | B | RC(O)Cl |
| MG-310 | BOP | B | $Ac_2O$ |
| MG-311 | BOP | B | HCl, dioxane |
| MG-312 | EDC | B | RC(O)Cl |
| MG-313 | — | B | $RCO_2H$, TBTU |
| MG-314 | TBTU | B | RC(O)Cl |
| MG-315 | BOP | B | RC(O)Cl |
| MG-316 | BOP | B | |
| MG-319 | TBTU | B | |
| MG-321 | TBTU | B | RC(O)Cl |
| MG-322 | TBTU | B | RC(O)Cl |
| MG-323 | — | B | $Ac_2O$ |
| MG-325 | TBTU | B | $RCO_2H$, TBTU |
| MG-328 | TBTU | B | RC(O)Cl |
| MG-329 | TBTU | B | RC(O)Cl |
| MG-332 | TBTU | B | NaH, MeI |
| MG-333 | TBTU | B | NaH, MeI |
| MG-334 | TBTU | B | NaH, MeI |
| MG-336 | TBTU | B | RC(O)Cl |
| MG-337 | TBTU | B | HCl, dioxane |
| MG-338 | EDC | B | RC(O)Cl |
| MG-339 | TBTU | B | HCl, dioxane |
| MG-340 | TBTU | B | HCl, dioxane |
| MG-341 | TBTU | B | $RCO_2H$, TBTU |
| MG-342 | — | B | $RNH_2$, TBTU |
| MG-343 | TBTU | B | $RCO_2H$, TBTU |
| MG-344 | BOP | B | $Ac_2O$ |
| MG-345 | EDC | B | RC(O)Cl |
| MG-346 | EDC | B | RC(O)Cl |
| MG-347 | EDC | B | $RS(O)_2Cl$ |
| MG-348 | TBTU | B | HCl, dioxane |
| MG-349 | TBTU | B | HCl, dioxane |
| MG-350 | TBTU | B | $PhCH_2NCO$ |
| MG-351 | EDC | B | — |
| MG-352 | TBTU | B | $RCO_2H$, TBTU |
| MG-353 | TBTU | B | RC(O)Cl |
| MG-354 | BOP | B | $RS(O)_2Cl$ |
| MG-356 | TBTU | B | — |
| MG-357 | TBTU | B | HCl, dioxane |
| MG-358 | TBTU | B | RC(O)Cl |
| MG-359 | TBTU | B | HCl, dioxane |
| MG-361 | TBTU | B | $RCO_2H$, TBTU |
| MG-362 | — | B | $PhCH_2NCO$ |
| MG-363 | TBTU | B | HCl, dioxane |
| MG-364 | — | B | $RCO_2H$, TBTU |
| MG-366 | TBTU | B | HCl, dioxane |
| MG-367 | — | B | RC(O)Cl |
| MG-368 | EDC | B | TBTU |
| MG-369 | TBTU | B | HCl, dioxane |

[a]A = $NaIO_4$, $NH_4OAc$, acetone-water; B = $i$-$BuB(OH)_2$, 1N HCl, MeOH-hexane. See Examples for detailed descriptions of procedures.

EXAMPLES

Example 1

N-(4-Morpholine)carbonyl-β-(1-naphthyl)-L-alanine-L-leucine boronic acid [MG-273]

A. (1S,2S,3R,5S)-Pinanediol N-Boc-β-(1-naphthyl)-L-alanine-L-leucine boronate

To a solution of (1S,2S,3R,5S)-pinanediol leucine boronate trifluoroacetate salt (664 mg, 1.76 mmol) and N-Boc-β-(1-naphthyl)-L-alanine (555 mg, 1.76 mmol) in DMF (10 mL) at 0° C. was added 1-ethyl-3-(3-dimethylaminopropyl) carbodiimide hydrochloride (EDC) (404 mg, 2.11 mmol), 1-hydroxybenzotriazole monohydrate (HOBT) (285 mg, 2.11 mmol), and N-methylmorpholine (NMM) (0.3 mL, 2.64 mmol). The mixture was allowed to warm to room temperature and stir overnight. The reaction was quenched with water (100 mL), and the mixture was extracted with $CH_2Cl_2$ (4×25 mL). The combined organic layers were washed with 5% aqueous HCl and saturated aqueous $NaHCO_3$, dried over anhydrous $MgSO_4$, filtered, and concentrated to give a yellow oil. Water was added and the resultant gummy precipitate was extracted with ether (3×25 mL). The organic layer was dried (anhydrous $MgSO_4$), filtered, and concentrated to afford the title compound (202 mg) as a white foam.

B. (1S,2S,3R,5S)-Pinanediol β-(1-Naphthyl)-L-alanine-L-leucine boronate trifluoroacetate salt To a solution of the product of Example 1A (930 mg, 1.38 mmol) in $CH_2Cl_2$ (10 mL) at 0° C. was added trifluoroacetic acid (5 mL) and thioanisole (1 mL). The reaction mixture was allowed to warm to room temperature. After 4 h, the reaction mixture was concentrated to dryness and dried in vacuo. The residue was used in the next reaction without further purification.

C. (1S,2S,3R,5S)-Pinanediol N-(4-morpholine)carbonyl-β-(1-naphthyl)-L-alanine-L-leucine boronate 4-Morpholinecarbonyl chloride (50 mL, 0.42 mmol) and triethylamine (150 mL, 1.08 mmol) were added to a solution of the product of Example 1B (0.25 g, 0.36 mmol) in $CH_2Cl_2$ (6 mL). After 24 h, additional morpholinecarbonyl chloride (50 mL) and triethylamine (150 mL) were added. After 2 days total reaction time, the reaction mixture was diluted with EtOAc, washed with 1N HCl and saturated aqueous $NaHCO_3$, dried over $MgSO_4$, filtered, and concentrated. Purification by flash chromatography (elution with 1:2 EtOAc/hexanes and 4:4:1 hexanes/EtOAc/MeOH) afforded the title compound (124 mg).

D. N-(4-Morpholine)carbonyl-β-(1-naphthyl)-L-alanine-L-leucine boronic acid

To a stirred solution of the product of Example 1C (124 mg, 0.21 mmol) in acetone (10 mL) was added aqueous $NH_4OAc$ (0.1 N, 5 mL, 1.0 mmol), followed by $NaIO_4$ (120 mg, 0.21 mmol). The reaction mixture was stirred at room temperature for 72 h, and then the acetone was evaporated. The aqueous layer was acidified to pH 3 with 1N HCl and extracted with EtOAc (3×20 mL). The combined organic layers were dried over anhydrous $MgSO_4$, filtered, and concentrated. The residue was purified by flash chromatography (elution with 1:1 hexane/EtOAc, 2:2:1 hexanes/EtOAc/MeOH, and 1:1:few drops MeOH:EtOAc:HOAc) to give the title compound (29 mg).

Example 2

N-Cbz-L-Leucine-L-leucine boronic acid [MG-274]

A. (1S,2S,3R,5S)-Pinanediol N-Cbz-L-leucine-L-leucine boronate

Benzotriazol-1-yloxytris(dimethylamino)phosphonium hexafluorophosphate (BOP reagent, 827 mg, 1.87 mmol) was added in one portion to a mixture of (1S,2S,3R,5S)-pinanediol leucine boronate trifluoroacetate salt (595 mg, 1.58 mmol), N-Cbz-L-leucine (500 mg, 1.87 mmol) in acetonitrile (30 mL) at room temperature. The mixture was stirred at room temperature for 2 hours. The reaction was quenched with brine (50 mL) and the mixture was extracted with EtOAc (3×50 mL). The combined organic layers were washed with aqueous 5% HCl, saturated aqueous $NaHCO_3$, and saturated aqueous NaCl, and then dried (anhydrous $MgSO_4$), filtered, and concentrated. The residue was purified by silica gel chromatography (elution with 20–30% acetone/hexanes) to afford the title compound (539 mg).

B. N-Cbz-L-Leucine-L-leucine boronic acid

By a procedure analogous to that described in Example 1D, the compound of Example 2A above (539 mg) was deprotected by treatment with sodium metaperiodate (1.2 g, 5.61 mmol) and aqueous $NH_4OAc$ (0.1 N, 10 mL, 1.0 mmol) to provide the title compound as a white solid (154 mg).

Example 3

β-(1-Naphthyl)-L-alanine-L-leucine boronic acid hydrochloride salt [MG-302] and β-(1-Naphthyl)-L-alanine-L-leucine boronic acid [MG-303]

A. (1S,2S,3R,5S)-Pinanediol β-(1-naphthyl)-L-alanine-L-leucine boronate hydrochloride salt To a solution of (1S,2S,3R,5S)-pinanediol β-(1-naphthyl)-L-alanine-L-leucine boronate trifluoroacetate salt (prepared as described in Example 1B, 536 mg, 0.93 mmol) in ether (2 mL) was added 10 mL of 1N HCl. The mixture was sonicated for several minutes. Ether was allowed to slowly evaporate. The resultant crystals were collected, washed with $H_2O$ and ether, and dried in vacuo to provide the title compound (300 mg).

B. β-(1-Naphthyl)L-alanine-L-leucine boronic acid hydrochloride salt; and β-(1-Naphthyl)-L-alanine-L-leucine boronic acid To the product of Example 3A (290 mg, 0.58 mmol) in a mixture of hexane (4 mL), MeOH (4 mL), and 1N HCl (1.3 mL) was added i-BuB(OH)$_2$ (71 mg, 0.70 mmol). The reaction mixture was stirred for 72 h at room temperature. The MeOH-$H_2O$ layer was washed with hexanes, and the MeOH was evaporated. The aqueous solution was made basic with NaOH and washed with ether-EtOAc (1:1). The aqueous layer was lyophilized to give 640 mg of a yellow solid. The solid was dissolved in MeOH, 4N HCl in 1,4-dioxane was added, and the solution was filtered to remove a white solid. The filtrate was concentrated and the residue was purified by reverse phase HPLC (elution with $CH_3CN$—$H_2O$) to afford 45 mg of MG-302 and 10 mg of MG-303.

Example 4

N-(4-Morpholine)carbonyl-(O-benzyl)-L-tyrosine-L-leucine boronic acid [MG-306]

A. N-Boc-O-Benzyl-L-tyrosine

A suspension of O-benzyl-L-tyrosine (3.12 g, 11.5 mmol) in a mixture of 1,4-dioxane (14 mL) and water (14 mL) was treated, in order, with triethylamine (5.0 mL, 35.9 mmol) and a solution of (Boc)$_2$O (2.86 g, 13.1 mmol) in 1,4- dioxane (12 mL). After 19 h, the reaction mixture was diluted with water (140 mL) and washed with ether. The aqueous layer was acidified with 1N citric acid (35 mL) and extracted with $CH_2Cl_2$ (2×100 mL). Additional citric acid (15 mL) was added to the aqueous layer, which was again extracted with $CH_2Cl_2$ (100 mL). The combined organic extracts were dried ($MgSO_4$), filtered, and concentrated to give the crude product (4.5 g), which was used directly in the next reaction.

B. (1S,2S,3R,5S)-Pinanediol N-Boc-(O-benzyl)-L-tyrosine-L-leucine boronate

To a stirred and cold (0° C.) solution of (1S,2S,3R,5S)-pinanediol β-(1-naphthyl)-L-alanine-L-leucine boronate trifluoroacetate salt (prepared as described in Example 1B, 3.03 g, 7.98 mmol), N-Boc-O-benzyl-L-tyrosine (2.97 g, 7.99 mmol), and TBTU (3.35 g, 8.84 mmol) in anhydrous DMF (30 mL) was added by syringe pump, at the rate of 1.9 mL/h, DIEA (4.2 mL, 24.1 mmol). After the addition was complete, the mixture was allowed to warm to room temperature over 30 min, and then it was added dropwise to 30 mL of rapidly stirring water. Additional water was added and the mixture was filtered. The collected solid was dissolved in MeOH, concentrated to near dryness and again added to rapidly stirring water (300 mL). The resultant white solid was collected by suction filtration, washed with water, frozen, and lyophilized to provide the title compound (4.49 g).

C. (1S,2S,3R,5S)-Pinanediol (O-benzyl)-L-tyrosine-L-leucine boronate

The product of Example 4B (4.47 g, 7.23 mmol) was dissolved in $CH_2Cl_2$ (40 mL) and cooled to 0° C. A solution of 4N HCl in dioxane (40 mL, 0.16 mol) was added and the reaction mixture was stirred at room temperature for 1.5 h. Concentration afforded a yellow solid, which was triturated with hexane-ether (1:1, 100 mL). Filtration afforded the title compound (3.65 g) as a pale yellow solid.

D. (1S,2S,3R,5S)-Pinanediol N-(4-morpholine)carbonyl-(O-benzyl)-L-tyrosine-L-leucine boronate By a procedure analogous to that described in Example 1C, the product of Example 4C (2.53 g, 4.56 mmol) was treated with 4-morpholinecarbonyl chloride (0.75 mL, 6.43 mmol) to provide the title compound (2.35 g) as a pale yellow solid.

E. N-(4-morpholine)carbonyl-(O-benzyl)-L-tyrosine-L-leucine boronic acid

The product of Example 4D (0.39 g, 0.62 mmol) was deprotected according to the procedure described in Example 3B to provide the title compound (146 mg) as a white solid.

Example 5

N-Methyl-N-Cbz-L-leucine-L-leucine boronic acid [MG-268]

A. N-Methyl-N-Cbz-L-leucine

To a solution of N-Cbz-leucine (1.38 g, 5.2 mmol) in THF (15 mL) at 0° C. was added methyl iodide (2.5 mL, 40.1 mmol). Sodium hydride (60% dispersion in oil, 0.6 g, 15 mmol) was added cautiously, and the resultant mixture was stirred at room temperature for 24 h. The reaction mixture was diluted with EtOAc (25 mL) and water (2 mL) was added dropwise. The mixture was concentrated to dryness, and the residue was partitioned between ether (15 mL) and water (50 mL). The organic layer was extracted with saturated aqueous $NaHO_3$ (25 mL), and the combined aqueous extracts were acidified to pH 2 with 3N HCl. The product was extracted with EtOAc (3×25 mL), dried over $MgSO_4$, filtered, and concentrated to afford the title compound (1.41 g) as a yellow solid.

B. (1S,2S,3R,5S)-Pinanediol N-methyl-N-Cbz-L-leucine-L-leucine boronate

By a procedure analogous to that described in Example 1A, the product of Example 5A (85.1 mg, 0.30 mmol) was coupled with (1S,2S,3R,5S)-pinanediol leucine boronate trifluoroacetate salt (105 mg, 0.28 mmol) in the presence of EDC (64 mg, 0.33 mmol), HOBT (45 mg, 0.33 mmol), and NMM (37 mg, 0.37 mmol) to provide, after purification by flash chromatography (elution with 3:2 hexanes/acetone), the title compound (85 mg).

C. N-Methyl-N-Cbz-L-leucine-L-leucine boronic acid

By a procedure analogous to that described in Example 1D, the product of Example 5B (85 mg, 0.16 mmol) was deprotected by treatment with $NaIO_4$ (104 mg, 0.485 mmol) and aqueous $NH_4OAc$ (0.1N, 5 mL, 0.5 mmol) in 10 mL of acetone to provide, after purification by flash chromatography (elution with 4:4:2 hexanes/acetone/MeOH), the title compound (21 mg).

Example 6

N-(4-Morpholine)carbonyl-β-(6-quinolinyl)-D, L-alanine-L-leucine boronic acid [MG-292]

A. β-(6-Quinolinyl)-D,L-alanine

N-Acetyl β-(6-quinolinyl)-D,L-alanine ethyl ester (728 mg, 2.55 mmol) was heated at reflux in 6N HCl (20 mL). After 20 h, the reaction mixture was concentrated to dryness and the residue was dried in vacuo to provide the title compound, which was used directly in the next reaction.

B. N-Boc-β-(6-Quinolinyl)-D,L-alanine

To the crude product of Example 6A in a stirred mixture of 1,4-dioxane (10 mL), water (10 mL), and 2N NaOH (5 mL) at 0° C. was added di-tert-butyl pyrocarbonate (556 mg, 2.55 mmol). The reaction mixture was allowed to warm to room temperature. After 23 h, the reaction mixture was acidified to pH 4 and extracted with EtOAc (3×50 mL) and n-BuOH (3×50 mL). The combined extracts were concentrated to provide the title compound, which was used directly in the next reaction.

C. (1S,2S,3R,5S)-Pinanediol N-Boc-β-(6-quinolinyl)-D, L-alanine-L-leucine boronate By a procedure analogous to that described in Example 2A, the product of Example 6B was coupled with (1S,2S,3R,5S)-pinanediol leucine boronate trifluoroacetate salt (943 mg, 2.5 mmol) in the presence of BOP reagent (1.33 g, 3 mmol) and triethylamine (0.37 mL, 2.62 mmol) to provide the title compound (343 mg).

D. (1S,2S,3R,5S)-Pinanediol β-(6-quinolinyl)-D, L-alanine-L-leucine boronate

The product of Example 6C (343 mg, 0.61 mmol) was treated with trifluoroacetic acid (7 mL) and thioanisole (1 mL) in $CH_2Cl_2$ (15 mL) at 0° C., as described in Example 1B, to provide the title compound.

E. (1S,2S,3R,5S)-Pinanediol N-(4-morpholine) carbonyl-β-(6-quinolinyl)-D,L-alanine-L-leucine boronate The product of Example 6D was coupled with 4-morpholinecarbonyl chloride (0.14 mL, 1.22 mmol) by a procedure analogous to that described in Example 1C to produce the title compound (112 mg).

F. N-(4-Morpholine)carbonyl-β-(6-quinolinyl)-D, L-alanine-L-leucine boronate

Deprotection of the product of Example 6E (153 mg, 0.27 mmol) was effected according to the procedure described in Example 3B. Purification by silica gel chromatography (elution with 50:50:10 hexanes/acetone/methanol) afforded the title compound (87 mg). The product was further purified by reverse phase HPLC; 5 mg of the title compound was recovered.

Example 7

N-(4Morpholine)carbonyl-β-(1-naphthyl)-L-alanine-L-leucine methylborinic acid [MG-3171]; and N-(4-Morpholine) carbonyl-β-(1-naphthyl)-L-alanine-L-leucine dimethylborane [MG-318]

To a suspension of MG-273 (prepared as described in Example 1, 101.5 mg, 0.23 mmol) in 3 mL of a 2:1 mixture of $Et_2O/CH_2Cl_2$ was added 1,3-propanediol (20.0 mL, 0.28 mmol). The resultant clear solution was stirred for 30 min at room temperature, and then anhydrous $MgSO_4$ was added. Stirring was continued for an additional 30 min, and then the mixture was filtered through a cotton plug and then through a 0.2 mm PTFE filter. The solution was concentrated, toluene (2 mL) was added, and the mixture was again concentrated to produce a white solid. Anhydrous THF (3 mL) was added, and the resultant solution was cooled to 0° C. MeLi (0.8 mL, 1.12 mmol) was added. After 10 min, the mixture was warmed to room temperature. After 20 min, the light red solution was cooled to 0° C., quenched with a few drops of water, and then diluted with 10 mL of 1N HCl. The colorless solution was extracted with $CH_2Cl_2$ (2×10 mL), and the combined extract was concentrated to afford a white solid. Purification by flash chromatography (elution with 2–4% $MeOH/CHCl_3$, followed by 10% $MeOH/CHCl_3$) afforded MG-317 (17.7 mg) and MG-318 (72.1 mg).

Example 8

N-Benzyl-(3R)-3-dioxyboryl-5-methylhexanamide [MG-342]

A. tert-Butyl-(3R)-3-[(1S,2S,3R,5S)-(pinanediyldioxy)boryl]-5-methylhexanoate

A 200-mL round-bottomed flask was charged with anhydrous THF (50 mL) and tert-butyl acetate (0.48 mL, 3.56 mmol). The solution was cooled to −78° C. under nitrogen, and LDA (1.5 M solution in cyclohexane, 2.2 mL, 3.3 mmol) was added by syringe over 8 min. The resultant solution was stirred for 10 min, and then a solution of (1S,2S,3R,5S)-pinanediol 1-bromo-3-methylbutylboronate (*Organometallics* 9:3171(1990))(1.04 g, 3.15 mmol) in anhydrous THF (15 mL) was added by cannula over 8 min. The reaction mixture was allowed to warm to room temperature and stir overnight. The pale pink solution was concentrated, and the residue was dissolved in 200 mL of ether. The solution was washed with saturated aqueous $NH_4Cl$ and saturated aqueous NaCl. Concentration gave a clear orange oil, which was purified by flash chromatography (elution with 2–3% EtOAc/hexanes) to afford the title compound (584 mg).

B. (3R)-3-[(1S,2S,3R,5S)-(pinanediyldioxy)boryl]-5-methylhexanoic acid

To a solution of the product of Example 8A (323 mg, 0.89 mmol) in $CH_2Cl_2$ (8 mL) was added trifluoroacetic acid (2.0 mL, 26 mmol). The resultant mixture was stirred at room temperature for 2 h. The reaction mixture was concentrated and dried overnight under high vacuum to produce a dark brown oil (309.3 mg).

C. N-Benzyl-(3R)-3-[(1S,2S,3R,5S)-pinanediyldioxy)boryl]-5-methylhexanamide

To a solution of the product of Example 8B (300 mg, 0.9 mmol) and TBTU (410 mg, 1.08 mmol) in anhydrous acetonitrile (5 mL) was added benzylamine (0.12 mL, 1.10 mmol), followed by diisopropylethylamine (0.50 mL, 2.9 mmol). The reaction mixture was stirred overnight at room temperature, and then was poured into water and extracted with EtOAc. The organic layer was washed with saturated aqueous $NaHCO_3$ and saturated aqueous NaCl. Concentration gave a dark brown oil, which was purified by flash chromatography (elution with 20% EtOAc/hexanes) to afford the title compound (232 mg) as a clear, colorless oil.

D. N-Benzyl-(3R)-3-dioxyboryl-5-methylhexanamide

The product of Example 8C (223 mg, 0.56 mmol) was deprotected according to the procedure described in Example 3B. Purification by flash chromatography (elution with 5% $MeOH/CHCl_3$) provided a pale yellow oil, which was dissolved in acetonitrile/MeOH. Water was added and the mixture was lyophilized overnight to produce the title compound (108 mg) as a fluffy white solid.

Example 9

N-Acetyl-1,2,3,4-tetrahydro-3-isoquinolinecarbonyl-L-leucine boronic acid [MG-310]

A. N-Boc-1,2,3,4-Tetrahydro-3-isoquinolinecarboxylic acid

A solution of 1,2,3,4-tetrahydro-3-isoquinolinecarboxylic acid (855 mg, 4.83 mmol), $(Boc)_2O$ (1.37 g, 6.28 mmol), and 1N NaOH (6 mL) in a mixture of t-BuOH (12 mL) and water (12 mL) was stirred overnight at room temperature. The reaction mixture was diluted with water (30 mL) and washed with ether-hexanes (1:1, 2×25 mL). The organic layer was back-extracted with 10% $NaHCO_3$. The combined aqueous layers were carefully acidified to pH 2–3 and extracted with EtOAc (3×30 mL). The combined organic extracts were washed with water and saturated aqueous NaCl, dried ($MgSO_4$), and concentrated to provide the title compound (1.27 g) as a white solid.

B. (1S,2S,3R,5S)-Pinanediol N-Boc-1,2,3,4-tetrahydro-3-isoquinolinecarbonyl-L-leucine boronate To a mixture of (1S,2S,3R,5S)-pinanediol-L-leucine boronate trifluoroacetate salt (1.14 g, 3.03 mmol), N-Boc-1,2,3,4-tetrahydro-3-isoquinolinecarboxylic acid (762 mg, 2.75 mmol), and BOP reagent (1.34 g, 3.03 mmol) in DMF (20 mL) was added, over a period of 2 h, DIEA (1.44 mL, 8.25 mmol). The resultant solution was stirred for 1 h after addition was complete. The reaction mixture was poured into water (300 mL) and extracted with EtOAc (3×75 mL). The combined organic extracts were washed with dilute aqueous HCl, half-saturated aqueous $NaHCO_3$, water, and saturated aqueous NaCl, dried ($MgSO_4$), and concentrated. The residue was purified by flash chromatography (elution with 20% EtOAc-hexanes) to provide the title compound (1.04 g) as a white foamy solid.

C. (1S,2S,3R,5S)-Pinanediol 1,2,3,4-tetrahydro-3-isoquinolinecarbonyl-L-leucine boronate hydrochloride salt The product of Example 9B (755 mg) was dissolved in $CH_2Cl_2$ (10 mL) and cooled to 0° C. A solution of 4N HCl in dioxane (8 mL, 0.03 mol) was added and the reaction mixture was stirred at room temperature. Concentration and trituration with ether-hexanes afforded the title compound (565 mg) as an off-white solid.

D. (1S,2S,3R,5S)-Pinanediol N-acetyl-1,2,3,4-tetrahydro-3-isoquinolinecarbonyl-L-leucine boronate The product of Example 9C (262 mg, 0.59 mmol) was treated at room temperature with $Ac_2O$ (0.085 mL, 0.89 mmol) and DIEA (0.18 mL, 1.36 mmol) in $CH_2Cl_2$ (5 mL). After 24 h, the reaction mixture was diluted with $CH_2Cl_2$ (20 mL), washed with 1N HCl, half-saturated $NaHCO_3$, and water, dried ($Na_2SO_4$), and concentrated. Purification by flash chromatography (elution with EtOAc-hexanes) afforded the title compound (271 mg) as a white foamy solid.

E. N-Acetyl-1,2,3,4-tetrahydro-3-isoquinolinecarbonyl-L-leucine boronic acid

By a procedure analogous to that described in Example 3B, the product of Example 9D (226 mg, 0.49 mmol) was deprotected to provide the title compound (131 mg) as a foamy, oily solid.

Example 10

N-(4Morpholine)carbonyl-β-(2-quinolyl)-L-alanine-L-leucine boronic acid [MG-315]

A. Diethyl (2-quinolylmethyl)acetamidomalonate

To a solution of 2(chloromethyl)quinoline monohydrochloride (5.0 g, 23.4 mmol) and diethyl acetamidomalonate (10.1 g, 46.7 mmol) in EtOH (60 mL) was added sodium methoxide (3.78 g, 70 mmol). The reaction mixture was heated at reflux for 6 h. The reaction mixture was cooled, filtered, and concentrated. The residue was dissolved in EtOAc (400 mL) and extracted with cold 4N HCl (3×150 mL). The aqueous layer was neutralized with 10N NaOH and extracted with EtOAc (3×200 mL). The combined organic extract was washed with water, dried (anhydrous $MgSO_4$), filtered, and concentrated to give the title compound (8.3 g).

B. N-Acetyl-β-(2-quinolyl)-D,L-alanine ethyl ester

To a solution of the product of Example 10A (8 g, 22.3 mmol) in EtOH (180 mL) was added 6.1N NaOH (6.5 mL, 40 mmol). After 2 h, 11.1N HCl (3.6 mL, 40 mmol) was added, and the reaction mixture was concentrated to dryness. The residue was suspended in 1,4-dioxane (200 mL) and the mixture was heated at reflux for 90 min. The reaction mixture was concentrated and the residue was purified by silica gel chromatography (elution with 30–50% acetone-hexanes) to provide to title compound (4.3 g).

C. N-Acetyl-β-(2-quinolyl)-L-alanine

The product of Example 10B (4.3 g, 15 mmol) was treated with Subtilisin Carlsberg (Sigma, 11.9 units/mg, 30 mg, 357 units) at room temperature in aqueous $NaHCO_3$ (0.2M, 120 mL). After 2 h, the reaction mixture was extracted with $CHCl_3$ (6×100 mL). The aqueous layer was concentrated to dryness to provide the title compound (3.5 g), which contained salts.

D. N-Boc-β-(2-Quinolyl)-L-alanine

A solution of the product of Example 10C (3.5 g, ca. 7.4 mmol ) in 6N HCl (40 mL) wa s heated a t reflux for 16 h. The solvent was removed and the residue was dried in vacuo.

To this residue was added 1,4-dioxane (20 mL), water (20 mL), and 2N NaOH (10 mL, 20 mmol). The solution was cooled to 0° C. and di-t-butyl pyrocarbonate (1.6 g, 7.5 mmol) was added. After 1 h at 0° C., the reaction mixture was warmed to room temperature and stirring was continued for 17 h. The reaction mixture was extracted with $CH_2Cl_2$ (100 mL) and n-BuOH (4×100 mL). The aqueous layer was acidified and again extracted with n-BuOH. The organic extract s were combined and concentrated to provide the title compound (1.6 g).

E. (1S,2S,3R,5S)-Pinanediol N-Boc-β-(2-quinolyl)-L-alanine-L-leucine boronate

By a procedure analogous to that described in Example 2A, the product of Example 10D (0.6 g, 1.9 mmol) was coupled with (1S,2S,3R,5S)-pinanediol leucine boronate trifluoroacetate salt (716 mg, 1.9 mmol) in the presence of BOP reagent (0.84 g, 1.9 mmol) and triethylamine (0.27 mL, 1.9mmol). Purification by silica gel chromatography (elution with 10–30% acetone-hexanes) afforded the title compound (194 mg).

F. (1S,2S,3R,5S)-Pinanediol N-(4-morpholine)carbonyl-β-(2-quinolyl)-L-alanine-L-leucine boronate The product of Example 10E (194 mg) was treated with trifluoroacetic acid (7 mL) and thioanisole (1 mL) as described in Example 1B. The resultant product was condensed with 4-morpholinecarbonyl chloride (568 mg, 3.8 mmol) as described in Example 2C. Purification by silica gel chromatography (elution with 20–50% acetone-hexanes) afforded the title compound (367 mg).

G. N-(4Morpholine)carbonyl-β-(2-quinolyl)-L-alanine-L-leucine boronic acid

The product of Example 10F (367 mg, 0.64 mmol) was deprotected according to the procedure described in Example 3B to provide the title compound (222 mg).

Example 11

N-Boc-1,2,3,4-tetrahydro-1-isoquinolinecarboxylic acid [precursor for the synthesis of MG-310]

A. 1,2,3,4-Tetrahydro-1-isoquinolinecarboxylic acid

A solution of 1-isoquinolinecarboxylic acid (1.67 g) in glacial acetic acid (25 mL) was hydrogenated at 60 p.s.i. over $PtO_2$ (270 mg). When the reaction was complete, the mixture was filtered through Celite, washing the solid pad with MeOH, and the filtrate was concentrated to dryness. The resultant white solid was triturated with cold water and filtered to provide the title compound (775 mg).

B. N-Boc-1,2,3,4tetrahydro-1-isoquinolinecarboxylic acid

The product of Example 11B (762 mg, 4.3 mmol) was treated with di-tert-butyl pyrocarbonate (1.13 g, 5.17 mmol) according to the procedure described in Example 6B to afford the title compound (886 mg), as a foamy white solid.

Example 12

Diethanolamine N-(4-morpholine)carbonyl-β-(1-naphthyl)-L-alanine-L-leucine boronate [MG-286]

To a solution of N-(4-morpholine)carbonyl-β-(1-naphthyl)-L-alanine-L-leucine boronic acid (prepared as described in Example 1, 97.4 mg, 0.22 mmol) in $CH_2Cl_2$ (4 mL) was added a solution of diethanolamine (25.5 mg, 0.24 mmol) in EtOAc (1 mL). The resultant solution was stirred at room temperature for 0.5 h. Anhydrous $Na_2SO_4$ (1.5 g) was added and stirring was continued for an additional 0.5 h. The reaction mixture was filtered and concentrated, and the crude product was purified by stirring in hot EtOAc (2 mL) and precipitation with hexanes (1 mL). The solid was collected, washed with hexanes, and dried to provide the title compound (106 mg).

Example 13

N-[3-(4-morpholine)carbonyl-2(R)-(1-naphthyl) methyl] propionyl-L-leucine boronic acid [MG-324]

A. 1-Naphthalenecarboxaldehyde

To a cold (−78° C.) solution of oxalyl chloride (6.9 mL, 0.079 mol) in dry $CH_2Cl_2$ (200 mL) was added dropwise dry DMSO (11.2 mL, 0.158 mol). The mixture was stirred for 10 min, and then a solution of 1-naphthalenemethanol (10.0 g, 0.063 mol) in dry $CH_2Cl_2$ (40 mL) was added over 15 min. The mixture was stirred for 10 min, and then $Et_3N$ (44 mL, 0.316 mol) was added slowly. The reaction mixture was allowed to warm to room temperature. After 3.5 h, to the pale yellow heterogeneous mixture was added 10% aqueous citric acid (30 mL) and water (100 mL). The organic phase was washed with water (100 mL) and saturated aqueous NaCl (100 mL), dried (anhydrous $MgSO_4$), filtered, and concentrated. Ether-hexane (1:1) was added, and the mixture was filtered. Concentration provided a pale orange oil (9.7 g).

B. Ethyl 3-(1-naphthyl)propenoate

To a solution of the product of Example 12A (9.7 g, 62 mmol) in $CH_2Cl_2$ (150 mL) was added at room temperature (carbethoxymethylene) triphenylphosphorane (25 g, 71 mmol). The resultant mixture was stirred for 1.5 h, and the homogeneous yellow solution was then concentrated to dryness. Ether-hexane (1:1) was added, the mixture was filtered, and the filtrate was concentrated to dryness to provide a pale orange oil (15.3 g).

C. Ethyl 3-(1-naphthyl)propionate

The product of Example 12B (15.3 g, 68 mmol) was dissolved in a mixture of EtOAc (100 mL) and MeOH (10 mL) and hydrogenated at 1 atm. over 10% Pd/C (0.5 g). The reaction was continued for 4 days, replacing the catalyst with fresh catalyst several times. The reaction mixture was filtered and concentrated to provide 13 g of a crude oil.

D. 3-(1-Naphthyl)propionic acid

To a solution of the product of Example 12C (13 g) in a mixture of THF (100 mL) and water (25 mL) was added 1N NaOH (75 mL, 75 mmol). The brown reaction mixture was stirred at room temperature overnight. The THF was removed, and the aqueous layer was washed with ether (2×50 mL). The aqueous layer was acidified to pH 2 with 6N HCl and the precipitated solid was collected, washed with water (100 mL), and lyophilized to give 9.3 g of a pale yellow solid.

E. 3-(1-Naphthyl)propionyl chloride

To a suspension of the product of Example 12D (4.0 g, 20 mmol) in $CH_2Cl_2$ (25 mL) at 0° C. was added oxalyl chloride (1.9 mL, 22 mmol) and DMF (0.1 mL). The reaction mixture was warmed to room temperature and then heated with a heat gun. Additional oxalyl chloride (0.5 mL) was added and heating was continued to produce a dark homogeneous mixture. The reaction mixture was concentrated, the residue was redissolved in $CH_2Cl_2$-hexane, and the resultant solution was filtered. Concentration afforded 4.9 g of a green liquid.

F. 4(S)-Isopropyl-3-[3-(1-naphthyl)-1-oxopropyl]-2-oxazolidinone

To a solution of (4S)-(−)-4-isopopyl-2-oxazolidinone (2.32 g, 18 mmol) in dry THF (50 mL) at −78° C. was added dropwise n-BuLi (2.5M in hexanes, 8 mL, 20 mmol). The heterogeneous white mixture was stirred at −78° C. for 30 min, and then a solution of the product of Example 12E (4.9 g, 20 mmol) in dry THF (25 mL) was added dropwise over 15–20 min. After 1.5 h, the reaction was quenched by the addition of 1N HCl (25 mL) and saturated aqueous NaCl (25 mL). The mixture was stirred at room temperature for 30 min, and then the THF was removed by rotary evaporation. The aqueous layer was extracted with EtOAc, and the combined organic extract was dried (anhydrous $MgSO_4$), filtered, and concentrated. The residue was filtered through a pad of silica gel (elution with 20% EtOAc-hexanes) to provide 2.8 g of a pale pink solid.

G. 3-[3-Benzyloxycarbonyl-2(R)-[(1-naphthyl)methyl]-1-oxopropyl]-4(S)-isopropyl-2-oxazolidinone To a solution of 1,1,1,3,3,3-hexamethyldisilazane (0.75 mL, 3.5 mmol) in dry THF (10 mL) at 0° C. was added n-BuLi (2.5M in hexanes, 1.45 mL, 3.6 mmol). After 10 min, the mixture was cooled to −78° C. and a solution of the product of Example 12F (1.0 g, 3.2 mmol) in dry THF (8 mL) was added dropwise. After 30–40 min, benzyl bromoacetate (0.75 mL, 4.8 mmol) was added. The mixture was stirred at −78° C. for 1 h, and at 0° C. for 5–10 min. The reaction was quenched by the addition of 1N HCl (10 mL), and the solution was extracted with ether. The combined organic extract was washed with saturated aqueous $NaHCO_3$ and saturated aqueous NaCl, dried anhydrous $MgSO_4$), filtered and concentrated. The wet solid was triturated with hexane-ether (1:1), filtered, and dried to give the title compound (0.6 g) as a white solid.

H. 3-[2(R)-(1-naphthyl)methyl]-3-[4(S)-isopropyl-2-oxazolidinoyl] propanoic acid To the product of Example 12G (600 mg, 1.3 mmol) was added MeOH (15 mL), EtOH (15 mL), EtOAc (5 mL), and $CH_2Cl_2$ (5 mL), followed by 10% Pd/C (100 mg). The reaction mixture was hydrogenated under 1 atm. $H_2$. the reaction mixture was filtered and concentrated. The residue was triturated with ether-hexanes, the solvents were removed, and the resultant white solid was dried in vacuo to give 480 mg of the title compound.

I. 4(S)-Isopropyl-3-[4-morpholino-2(R)-(1-naphthyl)methyl-1,4-dioxobutyl]-2-oxazolidinone To a solution of the product of Example 12H (473 mg, 1.28 mmol) in dry THF (25 mL) at 0° C. was added dropwise under nitrogen morpholine (130 mL, 1.47 mmol), diethyl pyrocarbonate (240 mL, 1.47 mmol), and triethylamine (220 mL, 1.6 mmol). After 2 h, the solvent was removed in vacuo, and the residue was washed with water and extracted with ether-EtOAc (1:1). The combined organic extract was dried (anhydrous $MgSO_4$), filtered, and concentrated. The residue was triturated with EtOAc-hexanes to provide the title compound (410 mg).

J. 3-(4-morpholine)carbonyl-2(R)-(1-naphthyl)methyl propionic acid

To a solution of the product of Example 12I (400 mg, 0.913 mmol) in a mixture of THF (8 mL) and water (2 mL) at 0° C. was added LiOH (80 mg, 1.9 mmol). The reaction mixture was stored at 0° C. overnight. The reaction mixture was concentrated to remove THF, 1N NaOH (20 mL) was added, and the mixture was washed with $CH_2Cl_2$ (15 mL). The aqueous layer was acidified to pH 2 with 1N HCl and extracted with $CH_2Cl_2$. The combined organic extract was dried (anhydrous $MgSO_4$), filtered, and concentrated. The residue was triturated with ether-hexanes, and the solvents were removed in vacuo to provide the crude product (240 mg) as a white foam.

K. (1S,2S,3R,5S)-Pinanediol N-[3-(4-morpholine)carbonyl-2(R)-(1-naphthyl)methyl]propionyl-L-leucine boronate To a solution of the product of Example 12J (230 mg, 0.7 mmol) in DMF (8 mL) at 0° C. was added (1S,2S,3R,5S)-pinanediol leucine boronate trifluoroacetate salt (293 mg, 0.77 mmol) and TBTU (293 mg, (0.77 mmol). To the resultant mixture was added slowly over 1.5 h diisopropylethylamine (365 mL, 2.1 mmol). After addition was complete, the reaction mixture was stirred for 30 min. Water (100 mL) was added, and the precipitated solid was collected, washed with water (50 mL), and lyophilized to provide the title compound (300 mg).

L. N-[3-(4-morpholin)carbonyl-2(R)-(1-naphthyl)methyl]propionyl-L-leucine boronic acid By a procedure analogous to that described in Example 3B, the product of Example 12K (300 mg, 0.522 mmol) was deprotected to provide the title compound (150 mg).

Example 14 trans-4-Phenoxy-L-proline-L-leucine boronic acid

[MG-349]

A. N-Carbobenzyloxy-trans-4-hydroxy-L-proline

According to the literature procedure (*J. Am. Chem. Soc.* 189 (1957)), trans-4-hydroxy-L-proline (5.12 g, 0.039 mol) was treated with benzyl chloroformate (8.5 mL, 0.06 mol) to provide the title compound (6.0 g) as a white solid.

B. N-Carbobenzyloxy-trans-4-hydroxy-L-proline methyl ester

To a solution of the product of Example 13A (1.08 g, 3.75 mmol) in acetonitrile (4 mL) at 0° C. was added dropwise DBU (0.62 mL, 4.12 mmol). After 5 min, MeI (0.28 mL, 4.5 mmol) was added. The reaction mixture was allowed to warm to room temperature and stir overnight. The solvent was removed, the residue was dissolved in ether-EtOAc (1:1, 30 mL), and the resultant solution was washed with 1N HCl, dilute aqueous NaHCO$_3$, water, and saturated aqueous NaCl. The organic layer was dried (anhydrous MgSO$_4$) and concentrated to provide the title compound (822 mg) as a light yellow oil.

C. N-Carbobenzyloxy-trans-4-phenoxy-L-proline methyl ester

To a mixture of the product of Example 13B (495 mg, 1.71 mmol), phenol (193 mg, 2.05 mmol), and triphenylphosphine (537 mg, 2.05 mmol) in THF (7 mL) at 0° C. was added over 1 h diethyl azodicarboxylate (0.32 mL, 2.05 mmol). The reaction mixture was allowed to warm to room temperature and stir overnight. The reaction mixture was concentrated, and the residue was dissolved in ether (8 mL) and allowed to stand at 0° C. overnight. The solution was decanted and the solids were washed with cold ether. The ethereal solution was concentrated, and the residue was purified by flash chromatography (elution with 10–30% EtOAc-hexanes) to provide the title compound (295 mg).

D. N-Carbobenzyloxy-trans-4-phenoxy-L-proline

The product of Example 13C (285 mg, 0.79 mmol) was dissolved in a mixture of 0.5N aqueous LiOH (20 mL) and MeOH (10 mL), and the resultant solution was stirred at room temperature overnight. The MeOH was removed in vacuo, and the aqueous layer was washed with ether (2×20 mL). The aqueous layer was cooled, acidified with 3N HCl, and extracted with EtOAc (3×20 mL). The combined organic extract was washed with water and saturated aqueous NaCl, dried (anhydrous MgSO$_4$), filtered, and concentrated to provide the title compound (251 mg) as a light yellow solid.

E. (1S,2S,3R,5S)-pinanedioN-Carbobenzyloxy-trans-4-phenoxy-L-proline-L-leucine boronate By a procedure analogous to that described in Example 12K, the product of Example 13D (250 mg, 0.72 mmol) was coupled with (1S,2S,3R,5S)-pinanediol leucine boronate trifluoroacetate salt (300 mg, 0.79 mmol) in the presence of TBTU (302 mg, 0.79 mmol) to provide the title compound (355 mg) as a white solid.

F. (1S,2S,3R,5S)-pinanediol trans-4-phenoxy-L-proline-L-leucine boronate

The product of Example 13E (343 mg) was hydrogenated for 20 h at 1 atm. over 10% Pd/C (45 mg) in EtOH (3 mL). The reaction mixture was filtered through Celite and concentrated to provide the title compound (272 mg).

G. trans-4-Phenoxy-L-proline-L-leucine boronic acid

By a procedure analogous to that described in Example 3B, the product of Example 13F (270 mg, 0.6 mmol) was deprotected to provide the title compound (130 mg) as a white solid.

Example 15

[(3S,5R)-4-[(8-quinolinesulfonyl)amino]-3-hydroxy-5-(1-naphthyl)pentanoyl]-L-leucine boronic acid A. (4S,5S)-1-Boc-4-hydroxy-5-(1-naphthyl)-pyrrolidin-2-one To a solution of N-Boc-β-(1-naphthyl)-L-alanine (1.4 g, 4.44 mmol), 2,2-dimethyl-1,3-dioxane-4,6-dione(704 mg, 4.88 mmol), and 4-DMAP (1.25 g, 10.21 mmol) in CH$_2$Cl$_2$ (40 mL) at 0° C. was added isopropenyl chloroformate (0.53 mL, 4.8 mmol). The reaction mixture was stirred for 1 h at 0° C. and for 2 h at room temperature. The reaction was quenched by the addition of aqueous KHSO$_4$. The organic layer was washed with water, dried (anhydrous MgSO$_4$), filtered, and concentrated. The residue was suspended in EtOAc (30 mL) and heated at reflux for 2 h. The solvent was removed in vacuo.

The residue was dissolved in CH$_2$Cl$_2$—HOAc (10:1, 30 mL), and sodium borohydride (310 mg, 8.21 mmol) was added at 0° C. The mixture was stirred for 1 h at 0° C. and for 15 h at room temperature. Water was added, and the organic layer was washed with saturated aqueous NaCl, dried (anhydrous MgSO$_4$), filtered, and concentrated. Purification by silica gel chromatography (elution with 20–30% acetone-hexanes) afforded the title compound (1.24 g).

B. (3S,5R)-4-(tert-butyloxycarbonyl)amino-3-hydroxy-5-(1-naphthyl)pentanoic acid The product of Example 14B (1.24 g, 3.64 mmol) was dissolved in acetone (15 mL) and aqueous NaOH (1M, 4 mL, 4 mmol) was added. The reaction mixture was stirred at room temperature for 2 h. The mixture was acidified with 10% HCl and extracted with EtOAc (3×60 mL). The combined organic extract was washed with water, dried (anhydrous MgSO$_4$), filtered, and concentrated. The residue was purified by silica gel chromatography (elution with 30–50% acetone-hexanes and 70:30:10 hexane:acetone:methanol) to give the title compound (0.61 g).

C. (1S,2S,3R,5S)-Pinanediol [(3S,5R)-4-(tert-butyloxycarbonyl) amino-3-hydroxy-5-(1-naphthyl) pentanoyl]-L-leucineboronate By a procedure analogous to that described in Example 2, the product of Example 14B (395 mg, 1.1 mmol) was coupled with (1S,2S,3R,5S)-pinanediol leucine boronate trifluoroacetate salt (415 mg, 1.1 mol) in the presence of BOP reagent (487 mg, 1.1 mmol) to afford the title compound (261 mg).

D. (1S,2S,3R,5S)-Pinanediol [(3S,5R)-4-(8-quinolinesulfonyl) amino-3-hydroxy-5-(1-naphthyl) pentanoyl]-L-leucineboronate The product of Example 14C (261 mg, 0.43 mmol) was dissolved in CH$_2$Cl$_2$ (10 mL) and treated at 0° C. with trifluoroacetic acid (5 mL) and thioanisole (1 mL). After 2 h, solvents were evaporated.

The residue was dissolved in CH$_2$Cl$_2$ (10 mL) and cooled to 0° C. 8-Quinolinesulfonyl chloride (98 mg, 0.43 mmol) and triethylamine (0.12 mL, 0.86 mmol) were added. The reaction mixture was stirred at 0° C. for 1 h and at room temperature for 15 h. The solvents were removed, water was added, and the product was extracted with EtOAc (3×50 mL). The combined organic extract was washed with saturated aqueous NaHCO$_3$ and saturated aqueous NaCl, dried (anhydrous MgSO$_4$), and concentrated. The residue was purified by silica gel chromatography (elution with 20–50% EtOAc-hexanes) to provide the title compound (152 mg).

E. [(3S,5R)-4-(8-quinolinesulfonyl)amino-3-hydroxy-5-(1-naphthyl)pentanoyl]-L-leucine boronic acid The product of Example 14D (152 mg, 0.22 mmol) was deprotected according to the procedure described in Example 3B to provide the title compound (12.7 mg).

Example 16 cis-3-Phenyl-D,L-proline-L-leucine boronic acid hydrochloride salt [MG-359]

A. Diethyl 1-acetyl-4-phenyl-2-pyrrolidinol-5,5-dicarboxylate

Sodium spheres (washed 3× with hexanes and dried in vacuo; 0.13 g, 5.7 mmol) were added to a solution of diethyl acetimidomalonate (12.2 g, 56.1 mmol) in absolute EtOH under nitrogen. After the sodium had dissolved, the solution was cooled in an ice bath and cinnamaldehyde (7.8 mL, 61.7 mmol) was added dropwise. The bath was removed and the reaction mixture was stirred overnight at room temperature. The solution was adjusted to pH 4 with acetic acid (~3 mL). Solvents were evaporated and the residue was purified by silica gel chromatography (elution with EtOAc) to give a yellow solid, which was recrystallized (benzene-hexane) to provide the title compound (14.1 g) as a white solid.

B. Diethyl 1-acetyl-3-phenylpyrrolidine-2,2-dicarboxylate

Trifluoroacetic acid (15.4 mL) was added slowly over 15 min to a solution of the product of Example 15A (7.0 g, 20.1 mmol) and triethylsilane (4.9 mL, 30.8 mmol) in $CHCl_3$ (40 mL). After 3 h, the solvents were evaporated and the residue was dissolved in EtOAc (150 mL), washed with water, 5% aqueous $NaHCO_3$, and saturated aqueous NaCl, dried (anhydrous $MgSO_4$), and concentrated to give 5.9 g of a colorless oil.

C. N-Acetyl-3-phenylproline ethyl ester

The product of Example 15B (5.9 g) was dissolved in 0.5N NaOH (200 mL) and the resultant solution was stirred at room temperature for 21 h. The solution was washed with EtOAc (75 mL) and then acidified to pH 2 with 3N HCl. The precipitated solids were extracted with $CHCl_3$. The organic layer was concentrated to give a gummy residue, which was dissolved in toluene (70 mL) and heated at 75° C. for 1 h. The solvent was evaporated to provide the title compound (4.2 g) as a light yellow oil.

D. N-Acetyl-trans-3-phenyl-D,L-proline; and N-acetyl-cis-3-phenyl-D,L-proline ethyl ester.

The product of Example 15C (4.2 g, 16 mmol) was dissolved 1M NaOEt in EtOH (100 mL) which contained 2 mL of ethyl trifluoroacetate as a water scavenger, and the resultant solution was heated at reflux for 2 h. The reaction mixture was cooled to room temperature, water (65 mL) was added, and the solution was stirred for 2.5 h. Most of the EtOH was removed by rotary evaporation and the aqueous solution was extracted with $CH_2Cl_2$. The aqueous layer was acidified with 3N HCl and extracted with EtOAc. The organic extract was washed with water and saturated aqueous NaCl, dried (anhydrous $MgSO_4$), and concentrated. The orange gummy solid was triturated with ether to provide a yellow solid, which was recrystallized (EtOAc-MeOH) to provide the acid (1.91 g) as light yellow crystals. Concentration of the $CH_2Cl_2$ extracts afforded the ester (396 mg) as an orange oil.

E. cis-3-Phenyl-D,L-proline hydrochloride salt

The ester obtained in Example 15D (375 mg) was hydrolyzed by heating at reflux in 6N HCl (5 mL) for 17 h. The cooled reaction mixture was washed with EtOAc and the aqueous layer was concentrated to dryness. Recrystallization (MeOH-ether) afforded the title compound (201 mg).

F. N-Boc-cis-3-Phenyl-D,L-proline

The product of Example 15E (189 mg, 0.84 mmol) was dissolved in a mixture of 2N NaOH (3 mL) and 1,4-dioxane (3 mL). tert-Butyl pyrocarbonate (218 mg, 1.0 mmol) was added and the reaction mixture was stirred overnight at room temperature. Dioxane was removed by rotary evaporation, water (30 mL) was added, and the mixture was washed with EtOAc. The aqueous phase was cooled to 0° C., acidified with 3N HCl, and extracted with EtOAc. The organic layer was washed with water and saturated aqueous NaCl, dried (anhydrous $MgSO_4$), and concentrated to give the title compound (199 mg).

G. (1S,2S,3R,5S)-Pinanediol N-Boc-cis-3-phenyl-D,L-proline-L-leucine boronate

By a procedure analogous to that described in Example 4B, the product of Example 15F (192 mg, 0.66 mmol) was coupled with (1S,2S,3R,5S)-pinanediol leucine boronate trifluoroacetate salt (274 mg, 0.73 mmol) in the presence of TBTU (277 mg, 0.73 mmol) to provide the title compound (286 mg).

H. cis-3-Phenyl-D,L-proline-L-leucine boronic acid hydrochloride salt

The product of Example 15G (262 mg) was dissolved in $CH_2Cl_2$ (5 mL) and treated at 0° C. with 4N HCl-dioxane (4 mL). After 2 h, the reaction mixture was concentrated to dryness, and the residue was treated with isobutylboronic acid (66 mg, 0.64 mmol) according to the procedure described in Example 3B to provide the title compound (71 mg) as a white solid.

Example 17 trans-3-Phenyl-D,L-proline-L-leucine boronic acid hydrochloride salt [MG-363]

A. N-Boc-trans-3-Phenyl-L-proline

By a procedure analogous to that described in Example 1A, N-acetyl-trans-3-phenyl-D,L-proline (prepared as described in Example 15D; 1.5 g, 6.44 mmol) was coupled with (S)-a-methylbenzylamine (0.92 mL, 7.08 mmol) in the presence of EDC (1.26 g, 7.08 mmol) and HOBT 9956 mg, 7.08 mmol). The diastereomeric products were separated by flash chromatography (elution with 1.5–2.5% HOAc-EtOAc). Fractions corresponding to the slower eluting band were concentrated to provide a clear, colorless oil (913 mg).

The oil (900 mg, 2.68 mmol) was dissolved in a mixture of HOAc (7 mL) and 8N HCl and the mixture was heated at reflux for 18 h. The mixture was concentrated to dryness. The residue was dissolved in water (30 mL), washed with EtOAc, and again concentrated to dryness.

The residue was redissolved in 1:1 water-1,4-dioxane (15 mL) and treated with tert-butyl pyrocarbonate (1.13 g, 5.20 mmol) by a procedure analogous to that described in Example 15F to provide the title compound (574 mg) as a white solid.

B. trans-3-Phenyl-L-proline-L-leucine boronic acid hydrochloride salt

By procedures analogous to those described in Examples 15G–H, the product of Example 16A (332 mg, 1.14 mmol) was coupled with (1S,2S,3R,5S)-pinanediol leucine boronate trifluoroacetate salt (452 mg, 1.20 mmol) and deprotected to provide the title compound (101 mg) as a white solid.

Example 18

Kinetic Experiments

Table II summarizes results from kinetic experiments that measured the inhibition of the 20S proteasome by compounds having the structure of compound (1) or (2). P, $AA^1$, $AA^2$, $AA^3$, and $Z^1$ and $Z^2$ represent the structures present on compound (1) or (2). The protocol for the kinetic assay described in Tables II–V is as described in Rock et al., *Cell* 78:761–771 (1994). In these tables, $K_i$ values are reported, which are dissociation constants for the equilibrium that is established when enzyme and inhibitor interact to form the enzyme: inhibitor complex. The reactions were performed using SDS-activated 20S proteasome from rabbit muscle. The substrate used was Suc-LLVY-AMC.

TABLE II

Inhibition of the 20S Proteasome by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | 20S K$_i$ (nM) |
|---|---|---|---|---|---|---|
| MG-261 | Cbz | L-Leu | L-Leu | L-Leu | pinane diol | 0.032 |
| MG-262 | Cbz | L-Leu | L-Leu | L-Leu | (OH)$_2$ | 0.035 |
| MG-264 | Cbz | — | L-Leu | L-Leu | pinane diol | 119.00 |
| MG-267 | Cbz | — | L-Nal | L-Leu | pinane diol | 0.100 |
| MG-268 | Cbz (N—Me) | — | L-Leu | L-Leu | (OH)$_2$ | 998.00 |
| MG-270 | Cbz | — | L-Nal | L-Leu | (OH)$_2$ | 0.083 |
| MG-272 | Cbz | — | D-(2-Nal) | L-Leu | (OH)$_2$ | 34.0 |
| MG-273 | Morph | — | L-Nal | L-Leu | (OH)$_2$ | 0.18 |
| MG-274 | Cbz | — | L-Leu | L-Leu | (OH)$_2$ | 3.0 |
| MG-278 | Morph | L-Leu | L-Leu | L-Leu | (OH)$_2$ | 0.14 |
| MG-282 | Cbz | — | L-His | L-Leu | (OH)$_2$ | 25.0 |
| MG-283 | Ac | L-Leu | L-Leu | L-Leu | (OH)$_2$ | 0.46 |
| MG-284 | (structure: phenyl-C(OMe)(CF$_3$)-C(O)-) | — | — | L-Leu | (OH)$_2$ | 1,200 |
| MG-285 | Morph | — | L-Trp | L-Leu | (OH)$_2$ | 3.0 |
| MG-286 | Morph | — | L-Nal | L-Leu | diethanolamine | 0.15 |
| MG-287 | Ac | — | L-Nal | L-Leu | (OH)$_2$ | 0.13 |
| MG-288 | Morph | — | L-Nal | D-Leu | (OH)$_2$ | 72.5 |
| MG-289 | Ms | — | L-(3-Pal) | L-Leu | (OH)$_2$ | 6.3 |
| MG-290 | Ac | — | L-(3-Pal) | L-Leu | (OH)$_2$ | 5.4 |
| MG-291 | Ms | — | L-Nal | L-Leu | diethanolamine | 0.28 |
| MG-292 | Morph | — | (quinolin-6-ylmethyl amino acid structure) | L-Leu | (OH)$_2$ | 6.0 |
| MG-293 | Morph | — | D-Nal | D-Leu | (OH)$_2$ | 2,300 |
| MG-294 | H | — | L-(3-Pal) | L-Leu | (OH)$_2$ | 152 |
| MG-295 | Ms | — | L-Trp | L-Leu | (OH)$_2$ | 5.8 |
| MG-296 | (8-Quin)-SO$_2$ | — | L-Nal | L-Leu | (OH)$_2$ | 1.7 |
| MG-297 | Ts | — | L-Nal | L-Leu | (OH)$_2$ | 0.17 |
| MG-298 | (2-Quin)-C(O) | — | L-Nal | L-Leu | (OH)$_2$ | 0.075 |
| MG-299 | (quinoxaline-2-carbonyl structure) | — | L-Nal | L-Leu | (OH)$_2$ | 0.14 |
| MG-300 | Morph | — | L-(3-Pal) | L-Leu | (OH)$_2$ | 1.3 |
| MG-301 | Ac | — | L-Trp | L-Leu | (OH)$_2$ | 1.3 |
| MG-302 | H | — | L-Nal | L-Leu | (OH)$_2$ | 7.5 |
| MG-303 | H.HCl | — | L-Nal | L-Leu | (OH)$_2$ | 3.9 |
| MG-304 | Ac | L-Leu | L-Nal | L-Leu | (OH)$_2$ | 0.022 |
| MG-305 | Morph | — | D-Nal | L-Leu | (OH)$_2$ | 189 |
| MG-306 | Morph | — | L-Tyr—(O—Bn) | L-Leu | (OH)$_2$ | 0.23 |
| MG-307 | Morph | — | L-Tyr | L-Leu | (OH)$_2$ | 0.51 |
| MG-308 | Morph | — | L-(2-Nal) | L-Leu | (OH)$_2$ | 0.72 |
| MG-309 | Morph | — | L-Phe | L-Leu | (OH)$_2$ | 0.82 |

TABLE II-continued

Inhibition of the 20S Proteasome by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | 20S K$_i$ (nM) |
|---|---|---|---|---|---|---|
| MG-310 | Ac | — | (tetrahydroisoquinoline-3-carbonyl) | L-Leu | (OH)$_2$ | 90 |
| MG-312 | Morph | — | L-(2-Pal) | L-Leu | (OH)$_2$ | 6.3 |
| MG-313 | (phenylpropanoyl) | — | — | L-Leu | (OH)$_2$ | 42 |
| MG-314 | (2-Quin)-C(O) | — | L-Phe | L-Leu | (OH)$_2$ | 0.19 |
| MG-315 | Morph | — | (quinolin-2-yl-alanyl) | L-Leu | (OH)$_2$ | 2.2 |
| MG-316 | H.HCl | — | (tetrahydroisoquinoline-3-carbonyl) | L-Leu | (OH)$_2$ | 22 |
| MG-317 | Morph | — | L-Nal | L-Leu | (OH)(CH$_3$) | 99 |
| MG-318 | Morph | — | L-Nal | L-Leu | (CH$_3$)$_2$ | 640 |
| MG-319 | H.HCl | — | L-Pro | L-Leu | (OH)$_2$ | 20 |
| MG-321 | Morph | — | L-Nal | L-Phe | (OH)$_2$ | 0.32 |
| MG-322 | Morph | — | L-homoPhe | L-Leu | (OH)$_2$ | 2.2 |
| MG-323 | Ac | — | — | L-Leu | (OH)$_2$ | 850 |
| MG-324 | (morpholinyl-naphthyl-succinyl) | — | — | L-Leu | H | 2.0 |
| MG-325 | (2-Quin)-C(O) | — | L-homoPhe | L-Leu | (OH)$_2$ | 2.8 |
| MG-328 | Bz | — | L-Nal | L-Leu | (OH)$_2$ | 0.088 |

TABLE II-continued

Inhibition of the 20S Proteasome by Boronic Ester and Acid Compounds
P—AA¹—AA²—AA³—B(Z¹)(Z²)

| Compound | P[a] | AA¹ | AA²[b] | AA³[c] | Z¹, Z² | 20S K$_i$ (nM) |
|---|---|---|---|---|---|---|
| MG-329 | cyclohexyl-C(O)- | — | L-Nal | L-Leu | (OH)$_2$ | 0.03 |
| MG-332 | Cbz (N—Me) | — | L-Nal | L-Leu | (OH)$_2$ | 0.95 |
| MG-333 | H.HCl | — | L-Nal | L-Leu | (OH)$_2$ | 2.1 |
| MG-334 | H.HCl (N—Me) | — | L-Nal | L-Leu | (OH)$_2$ | 1.1 |
| MG-336 | (3-Pyr)-C(O) | — | L-Phe | L-Leu | (OH)$_2$ | 0.25 |
| MG-337 | H.HCl | — | tetrahydroisoquinoline-C(O)- | L-Leu | (OH)$_2$ | 230 |
| MG-338 | (2-Quin)-C(O) | — | L-(2-Pal) | L-Leu | (OH)$_2$ | 1.4 |
| MG-339 | H.HCl | — | piperidine-C(O)- | L-Leu | (OH)$_2$ | 1,600 |
| MG-340 | H | — | pyroglutamyl- | L-Leu | (OH)$_2$ | 480 |
| MG-341 | (2-Pyz)-C(O) | — | L-Phe | L-Leu | (OH)$_2$ | 0.6 |
| MG-342 | Bn | — | β-leucyl amide | — | (OH)$_2$ | 9,700 |
| MG-343 | (2-Pyr)-C(O) | — | L-Phe | L-Leu | (OH)$_2$ | 0.42 |
| MG-344 | Ac | — | tetrahydro-β-carboline-C(O)- | L-Leu | (OH)$_2$ | 51 |
| MG-345 | Bz | — | L-(2-Pal) | L-Leu | (OH)$_2$ | 0.76 |

TABLE II-continued

Inhibition of the 20S Proteasome by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | 20S K$_i$ (nM) |
|---|---|---|---|---|---|---|
| MG-346 | cyclohexyl-C(=O)- | — | L-(2-Pal) | L-Leu | (OH)$_2$ | 1.1 |
| MG-347 | (8-Quin)-SO$_2$ | — | L-(2-Pal) | L-Leu | (OH)$_2$ | 29 |
| MG-348 | H.HCl | — | 4-hydroxy-pyrrolidine-2-carbonyl | L-Leu | (OH)$_2$ | 21 |
| MG-349 | H.HCl | — | 4-phenoxy-pyrrolidine-2-carbonyl | L-Leu | (OH)$_2$ | 18 |
| MG-350 | benzyl-NH-C(=O)- | — | L-Phe | L-Leu | (OH)$_2$ | 0.14 |
| MG-351 | H.HCl | — | L-(2-Pal) | L-Leu | (OH)$_2$ | 32 |
| MG-352 | PhCH$_2$CH$_2$-C(=O)- | — | L-Phe | L-Leu | (OH)$_2$ | 0.15 |
| MG-353 | Bz | — | L-Phe | L-Leu | (OH)$_2$ | 0.15 |
| MG-354 | (8-Quin)-SO$_2$ | — | — | naphthyl-substituted keto-amino acid | L-Leu | (OH)$_2$ | 28 |
| MG-356 | Cbz | — | L-Phe | L-Leu | (OH)$_2$ | 0.13 |
| MG-357 | H.HCl | — | piperidine-2-carbonyl | L-Leu | (OH)$_2$ | 23 |

TABLE II-continued

Inhibition of the 20S Proteasome by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | 20S K$_i$ (nM) |
|---|---|---|---|---|---|---|
| MG-358 | 3-furoyl | — | L-Phe | L-Leu | (OH)$_2$ | 0.17 |
| MG-359 | H.HCl | — | 3-phenyl-pyrrolidine-2-carbonyl | L-Leu | (OH)$_2$ | 5.5 |
| MG-361 | 3-pyrrolyl-C(O) | — | L-Phe | L-Leu | (OH)$_2$ | 0.14 |
| MG-362 | PhCH$_2$NHC(O) | — | — | L-Leu | (OH)$_2$ | 6,400 |
| MG-363 | H.HCl | — | 3-phenyl-pyrrolidine-2-carbonyl | L-Leu | (OH)$_2$ | 3.45 |
| MG-364 | PhCH$_2$CH$_2$C(O) | — | — | L-Leu | (OH)$_2$ | 1,500 |
| MG-366 | H.HCl | — | piperidine-2-carbonyl | L-Leu | (OH)$_2$ | 45.2 |
| MG-368 | (2-Pyz)-C(O) | — | L-(2-Pal) | L-Leu | (OH)$_2$ | 5.6 |

TABLE II-continued

Inhibition of the 20S Proteasome by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | 20S K$_i$ (nM) |
|---|---|---|---|---|---|---|
| MG-369 | H.HCl | — | azetidine-2-carbonyl | L-Leu | (OH)$_2$ | 24.2 |

$^a$Cbz = carbobenzyloxy; Morph = 4-morpholinecarbonyl; (8-Quin)SO$_2$ = 8-quinolinesulfonyl; (2-Quin)C(O) = 2-quinolinecarbonyl; Bz = benzoyl; (2-Pyr)-C(O) = 2-pyridinecarbonyl; (3-Pyr)-C(O) = 3-pyridinecarbonyl; (2-Pyz)-C(O) = 2-pyrazinecarbonyl.
$^b$Nal = β-(1-naphthyl)alanine; (2-Nal) = β-(2-naphthyl)alanine; (2-Pal) = β-(2-pyridyl)alanine; (3-Pal) = β-(3-pyridyl)alanine; homoPhe = homophenylalanine.
$^c$B(Z$^1$)(Z$^2$) takes the place of the carboxyl group of AA$^3$.

In Table III, P, AA$^1$, AA$^2$, AA$^3$, and X are substituents of the general formula: P—AA$^1$—AA$^2$—AA$^3$—X Table III demonstrates that dipeptide boronic acids have lower K$_i$ values than the corresponding dipeptide aldehydes.

TABLE III

Comparison of Dipeptide Boronic Acids to Dipeptide Aldehydes

| Cpd. | P | AA$^1$ | AA$^2$ | AA$^3$ | X | 20S K$_i$ (nM) |
|---|---|---|---|---|---|---|
| MG-105 | Z | — | L-Leu | L-Leu | CHO | 15,000 |
| MG-274 | Z | — | L-Leu | L-Leu | B(OH)$_2$ | 3.0 |

In Table IV, P, AA$^1$, AA$^2$, AA$^3$, and X are substituents of the general formula: P—AA$^1$—AA$^2$—AA$^3$—X.

Table IV demonstrates the markedly superior selectivity for the 20S proteasome over other proteases, e.g. Cathepsin B, exhibited by the boronic esters/acids as compared to the peptide aldehydes.

TABLE IV

Inhibition of the 20S Proteasome by Boronic Ester and Acid Compounds
P—AA$^1$—AA$^2$—AA$^3$—X

| Compound | P | AA$^1$ | AA$^2$ | AA$^3$ | X | 20S K$_i$ (nM) | Cathepsin B K$_i$ (nM) |
|---|---|---|---|---|---|---|---|
| MG-154 | Ac | L-Leu | L-Leu | L-Leu | CHO | 66.0 | 5.0 |
| MG-191 | Cbz | L-Trp | L-Leu | L-Leu | CHO | 0.38 | 0.54 |
| MG-262 | Cbz | L-Leu | L-Leu | L-Leu | B(OH)$_2$ | 0.035 | 6,100 |
| MG-273 | morpholinecarbonyl | — | L-Nal | L-Leu | B(OH)$_2$ | 0.18 | 200,000 |
| MG-296 | 8-quinolinesulfonyl | — | L-Nal | L-Leu | B(OH)$_2$ | 1.7 | 4,000 |
| MG-309 | morpholinecarbonyl | — | L-Phe | L-Leu | B(OH)$_2$ | 0.82 | 132,000 |

TABLE IV-continued

Inhibition of the 20S Proteasome by Boronic Ester and Acid Compounds
P—AA¹—AA²—AA³—X

| Compound | P | AA¹ | AA² | AA³ | X | 20S $K_i$ (nM) | Cathepsin B $K_i$ (nM) |
|---|---|---|---|---|---|---|---|
| MG-341 | pyrazine-2-carbonyl | — | L-Phe | L-Leu | B(OH)$_2$ | 0.6 | 160,000 |

The selectivity of boronic acid inhibitors of the proteasome is further demonstrated in Table V.

TABLE V

Selectivity of Boronic Ester and Acid Inhibitors of the 20S Proteasome

| Compound | 20S $K_i$ (nM) | Human Leukocyte Elastase $K_i$ (nM) | Cathepsin G $K_i$ (nM) | Human Pancreatic Chymotrypsin $K_i$ (nM) |
|---|---|---|---|---|
| MG-262 | 0.03 | 15 | 55 | 7 |
| MG-267 | 0.1 | 150 | 33,000 | 2,300 |
| MG-296 | 1.7 | 36 | 9,200 | 75 |
| MG-309 | 0.82 | 7,000 | 4,800 | 465 |
| MG-341 | 0.6 | 2,300 | 628 | 322 |

Example 19

Inhibition of Protein Degradation in C2C12 Cells

C2C12 cells (a mouse myoblast line) were labelled for 48 hrs with $^{35}$S-methionine. The cells were then washed and preincubated for 2 hrs in the same media supplemented with 2 mM unlabelled methionine. The media was removed and replaced with a fresh aliquot of the preincubation media containing 50% serum, and a concentration of the compound to be tested. The media was then removed and made up to 10% TCA and centrifuged. The TCA soluble radioactivity was counted. Inhibition of proteolysis was calculated as the percent decrease in TCA soluble radioactivity. From this data, an $EC_{50}$ for each compound was calculated.

Data for compounds of structure (1) or (2) are presented in Table VI.

TABLE VI

Inhibition of Protein Degradation in C2C12 Cells by Boronic Ester and Acid Compounds
P—AA¹—AA²—AA³—B(Z¹)(Z²)

| Compound | P$^a$ | AA¹ | AA²$^b$ | AA³$^c$ | Z¹, Z² | IC$_{50}$ (nM) |
|---|---|---|---|---|---|---|
| MG-262 | Cbz | L-Leu | L-Leu | L-Leu | (OH)$_2$ | 280 |
| MG-270 | Cbz | — | L-Nal | L-Leu | (OH)$_2$ | 730 |
| MG-272 | Cbz | — | D-(2-Nal) | L-Leu | (OH)$_2$ | 6,000 |
| MG-273 | Morph | — | L-Nal | L-Leu | (OH)$_2$ | 140 |
| MG-274 | Cbz | — | L-Leu | L-Leu | (OH)$_2$ | 340 |
| MG-278 | Morph | L-Leu | L-Leu | L-Leu | (OH)$_2$ | 7,500 |
| MG-282 | Cbz | — | L-His | L-Leu | (OH)$_2$ | 64,000 |
| MG-283 | Ac | L-Leu | L-Leu | L-Leu | (OH)$_2$ | 3,000 |
| MG-285 | Morph | — | L-Trp | L-Leu | (OH)$_2$ | 2,400 |
| MG-286 | Morph | — | L-Nal | L-Leu | diethanolamine | 95 |
| MG-287 | Ac | — | L-Nal | L-Leu | (OH)$_2$ | 106 |
| MG-289 | Ms | — | L-(3-Pal) | L-Leu | (OH)$_2$ | 10,830 |
| MG-290 | Ac | — | L-(3-Pal) | L-Leu | (OH)$_2$ | 10,240 |
| MG-292 | Morph | — | 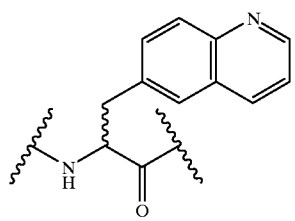 | L-Leu | (OH)$_2$ | 11,320 |
| MG-296 | (8-Quin)-SO$_2$ | — | L-Nal | L-Leu | (OH)$_2$ | 738 |
| MG-298 | (2-Quin)-C(O) | — | L-Nal | L-Leu | (OH)$_2$ | 230 |

TABLE VI-continued

Inhibition of Protein Degradation in C2C12 Cells by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | IC$_{50}$ (nM) |
|---|---|---|---|---|---|---|
| MG-299 | (quinoxaline-2-carbonyl) | — | L-Nal | L-Leu | (OH)$_2$ | 280 |
| MG-301 | Ac | — | L-Trp | L-Leu | (OH)$_2$ | 1,300 |
| MG-302 | H | — | L-Nal | L-Leu | (OH)$_2$ | 270 |
| MG-303 | H.HCl | — | L-Nal | L-Leu | (OH)$_2$ | 340 |
| MG-304 | Ac | L-Leu | L-Nal | L-Leu | (OH)$_2$ | 240 |
| MG-306 | Morph | — | L-Tyr—(O—Bn) | L-Leu | (OH)$_2$ | 130 |
| MG-307 | Morph | — | L-Tyr | L-Leu | (OH)$_2$ | 4,800 |
| MG-308 | Morph | — | L-(2-Nal) | L-Leu | (OH)$_2$ | 96 |
| MG-309 | Morph | — | L-Phe | L-Leu | (OH)$_2$ | 210 |
| MG-312 | Morph | — | L-(2-Pal) | L-Leu | (OH)$_2$ | 1,100 |
| MG-313 | (3-phenylpropanoyl) | — | — | L-Leu | (OH)$_2$ | 3,500 |
| MG-314 | (2-Quin)-C(O) | — | L-Phe | L-Leu | (OH)$_2$ | 130 |
| MG-315 | Morph | — | (quinolinyl-Ala) | L-Leu | (OH)$_2$ | 340 |
| MG-316 | H.HCl | — | (tetrahydroisoquinoline-3-carbonyl) | L-Leu | (OH)$_2$ | 21,000 |
| MG-319 | H.HCl | — | L-Pro | L-Leu | (OH)$_2$ | 14,000 |
| MG-321 | Morph | — | L-Nal | L-Phe | (OH)$_2$ | 2,400 |
| MG-322 | Morph | — | L-homoPhe | L-Leu | (OH)$_2$ | 380 |
| MG-325 | (2-Quin)-C(O) | — | L-homoPhe | L-Leu | (OH)$_2$ | 1,100 |
| MG-328 | Bz | — | L-Nal | L-Leu | (OH)$_2$ | 69 |
| MG-329 | (cyclohexylacetyl) | — | L-Nal | L-Leu | (OH)$_2$ | 48 |
| MG-332 | Cbz(N—Me) | — | L-Nal | L-Leu | (OH)$_2$ | 950 |
| MG-333 | H.HCl | — | L-Nal | L-Leu | (OH)$_2$ | 220 |
| MG-334 | H.HCl(N—Me) | — | L-Nal | L-Leu | (OH)$_2$ | 320 |
| MG-336 | (3-Pyr)-C(O) | — | L-Phe | L-Leu | (OH)$_2$ | 100 |
| MG-341 | (2-Pyz)-C(O) | — | L-Phe | L-Leu | (OH)$_2$ | 69 |
| MG-343 | (2-Pyr)-C(O) | — | L-Phe | L-Leu | (OH)$_2$ | 57 |
| MG-345 | Bz | — | L-(2-Pal) | L-Leu | (OH)$_2$ | 120 |

TABLE VI-continued

Inhibition of Protein Degradation in C2C12 Cells by Boronic Ester and Acid Compounds
P—AA$^1$—AA$^2$—AA$^3$—B(Z$^1$)(Z$^2$)

| Compound | P$^a$ | AA$^1$ | AA$^{2b}$ | AA$^{3c}$ | Z$^1$, Z$^2$ | IC$_{50}$ (nM) |
|---|---|---|---|---|---|---|
| MG-346 | cyclohexyl-C(O)- | — | L-(2-Pal) | L-Leu | (OH)$_2$ | 150 |
| MG-347 | (8-Quin)-SO$_2$ | — | L-(2-Pal) | L-Leu | (OH)$_2$ | 13,000 |
| MG-350 | PhCH$_2$-NH-C(O)- | — | L-Phe | L-Leu | (OH)$_2$ | 160 |
| MG-351 | H.HCl | — | L-(2-Pal) | L-Leu | (OH)$_2$ | 8,100 |

$^a$Cbz = carbobenzyloxy; Morph = 4-morpholinecarbonyl; (8-Quin)SO$_2$ = 8-quinolinesulfonyl; (2-Quin)C(O) = 2-quinolinecarbonyl; Bz = benzoyl; (2-Pyr)-C(O) = 2-pyridinecarbonyl; (3-Pyr)-C(O) = 3-pyridinecarbonyl; (2-Pyz)-C(O) = 2-pyrazinecarbonyl.
$^b$Nal = β-(1-naphthyl)alanine; (2-Nal) = β-(2-naphthyl)alanine; (2-Pal) = β-(2-pyridyl)alanine; (3-Pal) = b-(3-pyridyl)alanine; homoPhe = homophenylalanine.
$^c$B(Z$^1$)(Z$^2$) takes the place of the carboxyl group of AA$^3$.

Example 20
MG 273 Inhibits Corticosterone-Induced Cachexia in Rats

Rats were stabilized on a diet free from 3-methylhistidine and then placed in metabolic cages for collection of 24-hour urine samples. After two days of urine collections to determine basal 3-methylhistidine output, the rats were treated with daily subcutaneous injections of corticosterone (100 mg/kg). Starting on the second day of corticosterone treatment, some of the rats were also treated with MG 273, administered via a subcutaneous osmotic pump at a dose rate of approximately 120 μg/kg body weight/day. Control rats received vehicle only [25% DMSO/75% PEG (200)], administered in a similar fashion. FIG. 1 shows that treatment with MG 273 reduced the urinary output of 3-methylhistidine, which was induced in response to corticosterone treatment.

Example 21
MG 273 Inhibits the Activation of NF-κB

Figure 2:
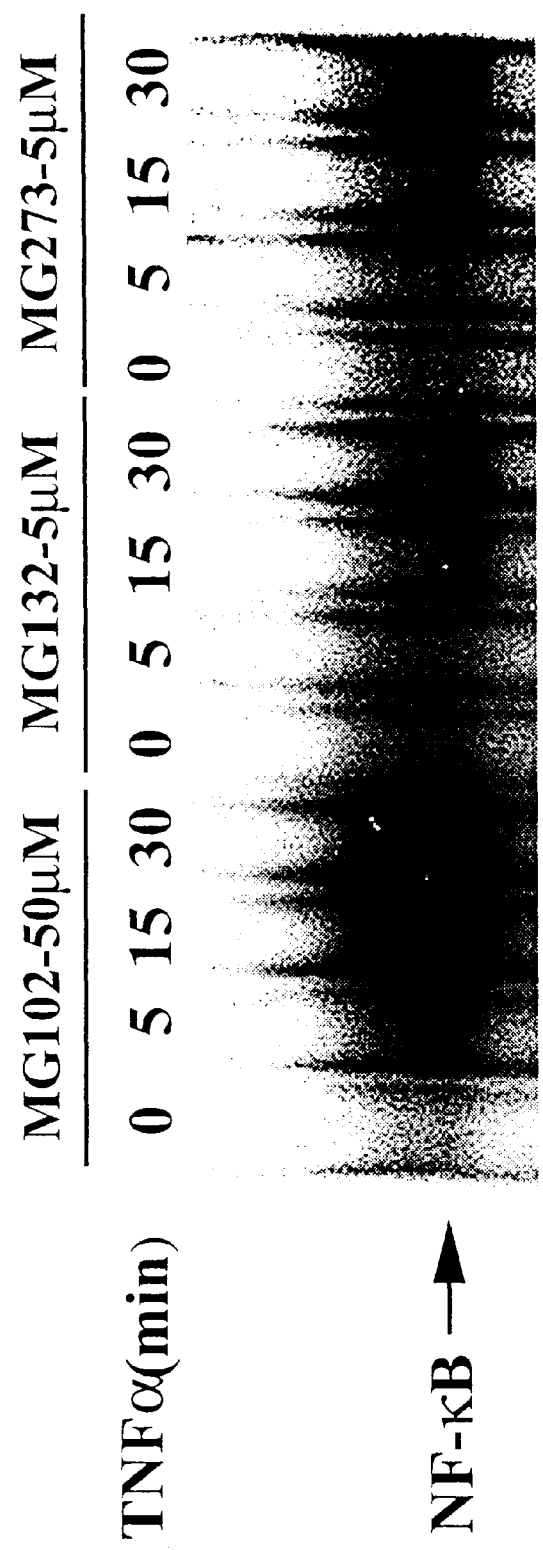
FIG. 2. NF-κB binding activity.

This assay was performed as previously described (Palombella, et al. Cell, 78:773–785 (1994). MG63 osteosarcoma cells were stimulated by treatment with TNF-α for the designated times. Whole cell extracts were prepared and analyzed by electrophoretic mobility shift assay using the PRDII probe from the human IFN-β gene promoter. FIG. 2 shows that NF-κB binding activity was inhibited by pretreatment for 1 hour with MG 273. An aldehyde inhibitor of the proteasome, MG 132 (Cbz-L-Leu-L-Leu-L-Leu-H), also inhibited NF-κB binding activity, whereas MG 102 (Ac-L-Leu-L-Leu-L-Met-H), which is inactive against the 20S proteasome, did not inhibit NF-κB binding activity.

Example 22
MG 273 Inhibits Expression of Cell Adhesion Molecules on HUVE Cells

Figure 3:
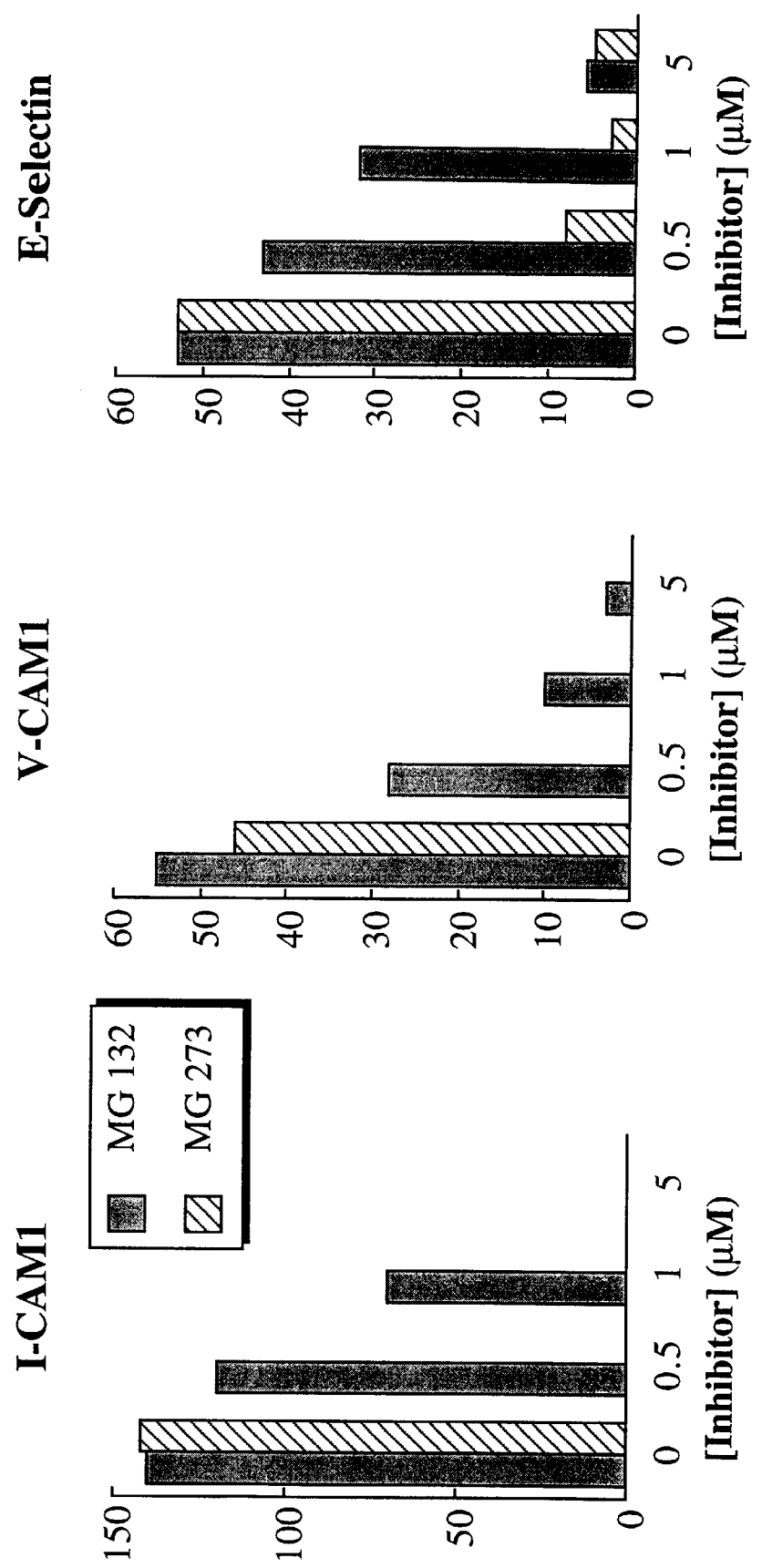
FIG. 3. Inhibition by MG 273.

HUVECs in microtiter plates were exposed to the indicated concentrations of inhibitor for 1 hour, prior to the addition of 100 U/mL TNF-α. Cell surface binding assays were performed at 4° C., using saturating concentrations of monoclonal antibodies specific for the cell adhesion molecules (Becton Dickenson) and fluorescent-conjugated F(ab')$_2$ goat anti-murine IgG (Caltag Labs, San Francisco, Calif.). Fluorescent immunoassays for E-selectin and I-CAM were performed at 4 hours, those for V-CAM at 16 hours. FIG. 3 shows that cell-surface expression I-CAM, V-CAM, and E-selectin on TNF-α stimulated HUVECs is significantly inhibited by MG 273 at concentrations of 0.5 μM or above.

Example 23
Boronic Acid Compounds Block the DTH Response in Mice

Naive mice were sensitized by the application of 20 μL of a 0.5% (v/v) solution of 2,4-dinitrofluorobenzene in 4:1 acetone/olive oil to both of the rear limb footpads. This procedure is performed on two consecutive days, which are referred to as days 0 and 1.

The efferent phase of the contact sensitivity response was elicited on day 5 by the application of 10 μL of a 0.2% (v/v) solution of 2,4-dinitrofluorobenzene in 4:1 acetone/olive oil to both sides of the left ear. The contralateral control ear was treated on both sides with 10 μL of vehicle only. The mice were lightly anaesthetized for this procedure by the intraperitoneal (i.p.) injection of a mixture of ketamine (80 mg/kg, Henry Schein) and xylazine (16 mg/kg, Henry Schein).

Test compounds were administered orally as a suspension in 0.5% methylcellulose (4000 centipoises Fisher Scientific) 30 minutes prior to the application of the challenge dose of 2,4-dinitrofluorobenzene to the ears. The dose was delivered in a final volume of 0.5 mL using a 24 gauge 1 inch malleable feeding needle with a 1.25 mm ball tip (Roboz Surgical).

Approximately 18 hours after the challenge, ear swelling was determined by measuring both the control and the experimental ear using a Mitutoyo Digital micrometer. The absolute difference in thickness of the experimental (left) ears vs. the control (right) ears was determined for each treatment group. Efficacy was determined by comparing this difference in thickness to the difference calculated for the vehicle control group. Test results are provided in Table VII.

TABLE VII

Inhibition of the DTH Response in Mice

| Compound | Dose (mg/kg) | % Inhibition |
|---|---|---|
| MG 296 | 50 | 60 |
| MG 309 | 3 | 40 |
| MG 341 | 3 | 90 |

All publications and U.S. patent applications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A compound of the structure:

$$P-N(R)-[B^1(R^1)-X^1]_A-CH(R^2)-X^2-CH(R^3)-B(Z^1)(Z^2)$$

where

P is, $$R^7-C(=O)-$$

or $$R^7-S(=O)_2-$$

where $R^7$ is selected from the group consisting of

[structures: 8-quinolinyl, 2-quinolinyl, quinoxalinyl, 3-methylpyridinyl, pyrazinyl, 2-pyridinyl, 3-methylfuranyl, 3-methylpyrrolyl]

or P is

[morpholinylcarbonyl structure]

$X^2$ is selected from the group consisting of

—C(=O)—NH—, —CH$_2$—NH—, —CH(OH)—CH$_2$—,
—CH(OH)—CH(OH)—, —CH(OH)—CH$_2$—NH—,
—CH=CH—, —C(=O)—CH$_2$—,
—S(=O)$_2$—NH—, —S(=O)$_2$—CH$_2$—, and
—CH(OH)—CH$_2$—C(=O)—NH—;

R is hydrogen or alkyl;

$R^2$ and $R^3$ are independently selected from the group consisting of hydrogen, alkyl, cycloalkyl, aryl, heterocycle and —CH$_2$—R$^5$,
  where $R^5$ is aryl, aralkyl, alkaryl, cycloalkyl, heterocycle or —Y—R$^6$,
  where Y is a chalcogen, and $R^6$ is alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

2. A compound of claim 1, wherein P is N-morpholinylcarbonyl.

3. A compound of claim 1, wherein $X^2$ is —C(O)NH—.

4. A compound of claim 1, wherein $R^2$ and $R^3$ are independently selected from the group consisting of alkyl and —CH$_2$R$^5$, wherein $R^5$ is as defined in claim 1.

5. A compound of claim 1, wherein $R^2$ and $R^3$ are independently selected from the group consisting of $C_{1-4}$ alkyl or —CH$_2$R$^5$, wherein $R^5$ is selected from the group consisting of cycloalkyl, aryl or heterocycle.

6. A compound of claim 1, wherein $R^3$ is isobutyl and $R^2$ is —CH$_2$R$^5$, wherein $R^5$ is $C_{5-10}$ aryl where one or more ring carbon atoms can be replaced by O, N or S.

7. A compound of claim 1, wherein $R^2$ is:

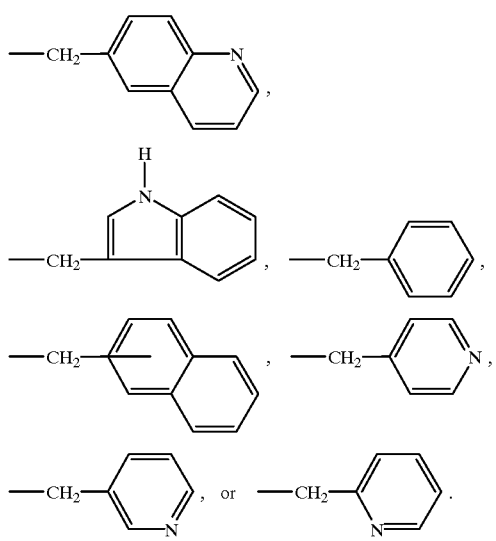

8. A compound of claim 1, wherein $Z^1$ and $Z^2$ are both hydroxy.

9. A compound of claim 1, wherein $Z^1$ and $Z^2$ together form a moiety derived from a dihydroxy compound selected from the group consisting of pinacol, perfluoropinacol, pinanediol, ethylene glycol, diethylene glycol, 1,2-cyclohexanediol, 1,3-propanediol, 2,3-butanediol, glycerol and diethanolamine.

10. A compound of claim 1, wherein $X^2$ is —C(O)—NH—;

R is hydrogen or alkyl;

$R^3$ is isobutyl;

$R^2$ is —CH$_2$R$^5$, wherein $R^5$ is $C_{5-10}$ aryl where one or more ring carbon atoms can be replaced by O, N or S; and $Z^1$ and $Z^2$ are both hydroxy, or together $Z^1$ and $Z^2$ form a moiety derived from a dihydroxy compound selected from the group consisting of pinacol, perfluoropinacol, pinanediol, ethylene glycol, diethylene glycol, 1,2-cyclohexanediol, 1,3-propanediol, 2,3-butanediol, glycerol and diethanolamine.

11. The compound of claim 1, wherein said compound is one of:

N-(2-pyridine)carbonyl-L-phenylalanine-L-leucine boronic acid,

N-(2-quinoline)carbonyl-L-phenylalanine-L-leucine boronic acid,

N-(3-furoyl)-L-phenylalanine-L-leucine boronic acid,

N-(2-pyrrolyl)carbonyl-L-phenylalanine-L-leucine boronic acid, or

N-(8-quinoline)sulfonyl-L-phenylalanine-L-leucine boronic acid.

12. A compound of claim 1 selected from the group consisting of:

N-(4-morpholine)carbonyl-β-(1-naphthyl)-L-alanine-L-leucine boronic acid,

N-(8-quinoline)sulfonyl-β-(1-naphthyl)L-alanine-L-leucine boronic acid,

N-(2-pyrazine)carbonyl-L-phenylalanine-L-leucine boronic acid,

N-(2-quinoline)sulfonyl-L-homophenylalanine-L-leucine boronic acid,

N-(3-Pyridine)carbonyl-L-phenylalanine-L-leucine boronic acid, and

N-(4-Morpholine)carbonyl-L-phenylalanine-L-leucine boronic acid.

13. A compound of the structure:

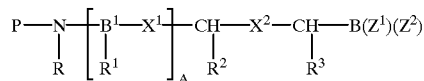

where

P is H or an amino-group-protecting moiety;

$X^2$ is selected from the group consisting of

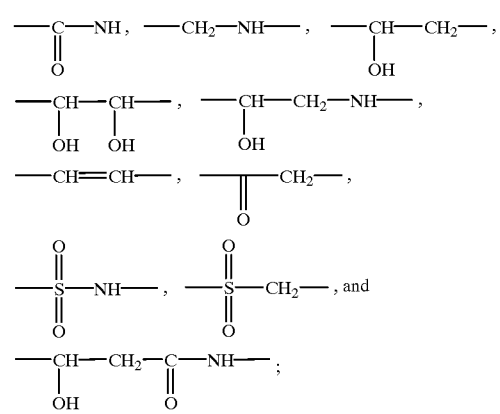

R is hydrogen or alkyl;

$R^3$ is selected from the group consisting of hydrogen, alkyl, cycloalkyl, aryl, heterocycle and —CH$_2$—R$^5$, $R^2$ is naphthylmethyl, pyridylmethyl, or quinolylmethyl, $R^5$ is aryl, aralkyl, alkaryl, cycloalkyl, heterocycle or —Y—R$^6$, where Y is a chalcogen, and $R^6$ is alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

14. A compound of claim 13, wherein $X^2$ is —C(O)NH—.

15. A compound of claim 13, wherein $R^3$ is isobutyl.

16. A compound of claim 13, wherein $Z^1$ and $Z^2$ are both hydroxy.

17. A compound of claim 13, wherein $Z^1$ and $Z^2$ together form a dihydroxy moiety selected from the group consisting of pinacol, perfluoropinacol, pinanediol, ethylene glycol, diethylene glycol, 1,2-cyclohexanediol, 1,3-propanediol, 2,3-butanediol, glycerol and diethanolamine.

18. A compound of claim 13, wherein $X^2$ is —C(O)—NH—;

R is hydrogen or alkyl;

$R^3$ is isobutyl; and $Z^1$ and $Z^2$ are both hydroxy, or together $Z^1$ and $Z^2$ form a moiety derived from a dihydroxy compound selected from the group consisting of pinacol, perfluoropinacol, pinanediol, ethylene glycol, diethylene glycol, 1,2-cyclohexanediol, 1,3-propanediol, 2,3-butanediol, glycerol and diethanolamine.

19. A method for reducing the rate of muscle protein degradation in a cell comprising contacting said cell with a proteasome inhibitor of the structure:

$$P-N(R)-[B^1(R^1)-X^1]_A-CH(R^2)-X^2-CH(R^3)-B(Z^1)(Z^2)$$

where

P is H or an amino-group-protecting moiety;

$X^2$ is selected from the group consisting of

—C(=O)—NH—, —CH$_2$—NH—, —CH(OH)—CH$_2$—, —CH(OH)—CH(OH)—, —CH(OH)—CH$_2$—NH—, —CH=CH—, —C(=O)—CH$_2$—, —S(=O)$_2$—NH—, —S(=O)$_2$—CH$_2$—, and —CH(OH)—CH$_2$—C(=O)—NH—;

R is hydrogen or alkyl;

$R^2$ and $R^3$ are independently selected from the group consisting of hydrogen, alkyl, cycloalkyl, aryl, heterocycle and —CH$_2$—R$^5$, heterocycle, or -chalcogenalkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

20. The method of claim 19 wherein P is $R^7$—C(=O)—, $R^7$—C(=S)—, $R^7$—NH—C(=O)—, or $R^7$—O—C(=O)— and $R^7$ is alkyl, aryl, alkaryl, aralkyl, or if P is $R^7$—C(=O)— or $R^7$—S(=O)$_2$—, heterocycle.

21. The method of claim 19 wherein $X^2$ is

—C(=O)—NH—.

22. The method of claim 19 wherein $R^2$ selected from the group consisting of alkyl and —CH$_2$—R$^5$, where $R^5$ is aryl, alkaryl, cycloalkyl, or heterocycle.

23. The method of claim 19 wherein the proteasome inhibitor is selected from the group consisting of:

N-(4-morpholine)carbonyl-β-(1-naphthyl)-L-alanine-L-leucine boronic acid,

N-(8-quinoline)sulfonyl-β-(1-naphthyl)L-alanine-L-leucine boronic acid,

N-(2-pyrazine)carbonyl-L-phenylalanine-L-leucine boronic acid,

N-(2-quinoline)sulfonyl-L-homophenylalanine-L-leucine boronic acid,

N-(3-Pyridine)carbonyl-L-phenylalanine-L-leucine boronic acid, and

N-(4-Morpholine)carbonyl-L-phenylalanine-L-leucine boronic acid.

24. The method of claim 19, wherein P is $R^7$—C(=O)— or $R^7$—S(=O)$_2$— and $R^7$ is alkyl, aryl, aralkyl or heterocycle.

25. The method of claim 24, wherein $R^7$ is

H$_3$C—, 8-methylquinolinyl, phenyl-CH$_2$—CH$_2$—, 4-methylphenyl, 2-methylquinolinyl, 2-methylquinoxalinyl, cyclohexyl, 3-methylpyridinyl, pyrazinyl, pyridinyl, phenyl,

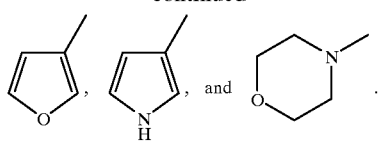

26. The method of claim 19, wherein $R^2$, or $R^3$ is arylalkyl of 6 to 14 carbon atoms, wherein 1 or more carbon is replaced by oxygen, nitrogen, or sulfur.

27. The method of claim 26, wherein $R^2$, or $R^3$ is

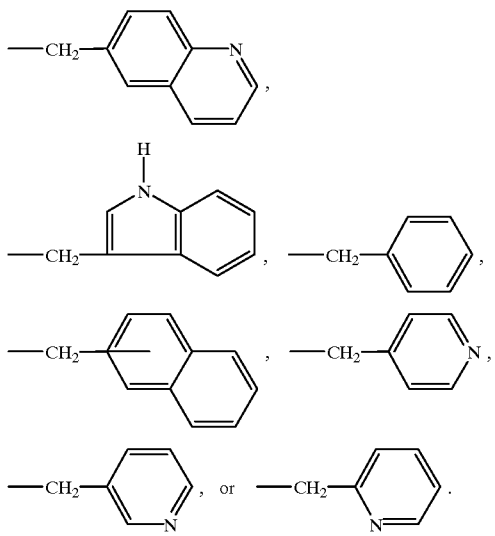

28. A method for reducing the rate of intracellular protein breakdown comprising contacting cells with a proteasome inhibitor of the structure:

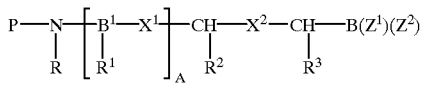

where

P is H or an amino-group-protecting moiety;
$X^2$ is selected from the group consisting of

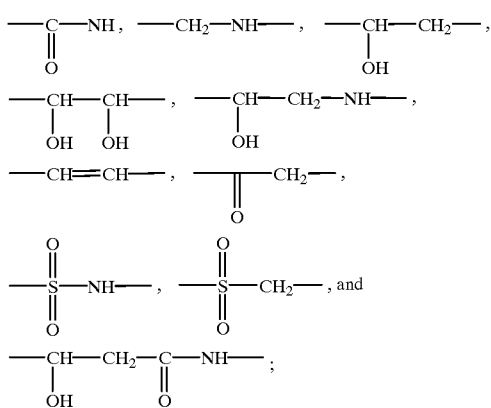

R is hydrogen or alkyl;

$R^2$ and $R^3$ are independently selected from the group consisting of hydrogen, alkyl, cycloalkyl, aryl, heterocycle and —$CH_2$—$R^5$,
  where $R^5$ is aryl, aralkyl, alkaryl, cycloalkyl, heterocycle, or -chalcogen-alkyl;
$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and
A is 0.

29. A method for reducing the rate of degradation of p53 protein in a cell comprising administering to said cell a proteasome inhibitor of the structure:

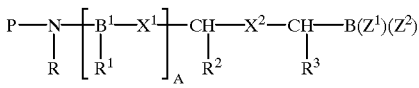

where
P is H or an amino-group-protecting moiety;
$X^2$ is selected from the group consisting of

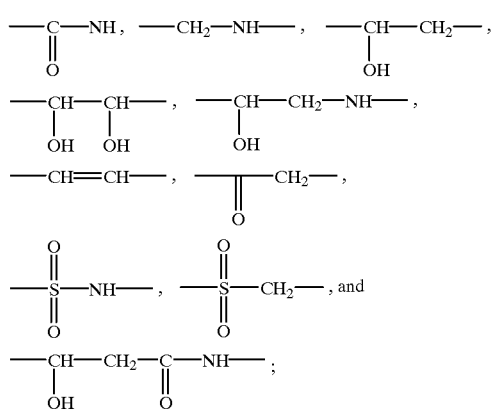

R is hydrogen or alkyl;
$R^2$ and $R^3$ are independently selected from the group consisting of hydrogen, alkyl, cycloalkyl, aryl, heterocycle and —$CH_2$—$R^5$,
  where $R^5$ is aryl, aralkyl, alkaryl, cycloalkyl, heterocycle, or -chalcogen-alkyl;
$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and
A is 0.

30. A method for inhibiting cyclin degradation in a cell comprising contacting said cell with a proteasome inhibitor of the structure:

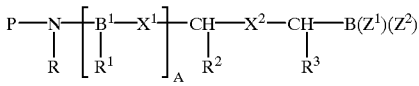

where
P is H or an amino-group-protecting moiety;

$X^2$ is selected from the group consisting of $$-\underset{O}{\overset{\|}{C}}-NH-, \quad -CH_2-NH-, \quad -\underset{OH}{\overset{|}{CH}}-CH_2-,$$

$$-\underset{OH}{\overset{|}{CH}}-\underset{OH}{\overset{|}{CH}}-, \quad -\underset{OH}{\overset{|}{CH}}-CH_2-NH-,$$

$$-CH=CH-, \quad -\underset{\overset{\|}{O}}{\overset{}{\underset{|}{C}}}-CH_2-,$$

$$-\underset{\overset{\|}{O}}{\overset{\overset{O}{\|}}{S}}-NH-, \quad -\underset{\overset{\|}{O}}{\overset{\overset{O}{\|}}{S}}-CH_2-, \text{ and}$$

$$-\underset{OH}{\overset{|}{CH}}-CH_2-\underset{O}{\overset{\|}{C}}-NH-;$$

R is hydrogen or alkyl;

$R^2$ and $R^3$ are independently selected from the group consisting of hydrogen, alkyl, cycloalkyl, aryl, heterocycle and $-CH_2-R^5$,
where $R^5$ is aryl, aralkyl, alkaryl, cycloalkyl, heterocycle, or -chalcogen-alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

31. A method for inhibiting antigen presentation in a cell comprising administering to said cell a proteasome inhibitor of the structure:

$$P-\underset{R}{\overset{}{\underset{|}{N}}}-\left[\underset{R^1}{\overset{}{\underset{|}{B^1}}}-X^1\right]_A-\underset{R^2}{\overset{}{\underset{|}{CH}}}-X^2-\underset{R^3}{\overset{}{\underset{|}{CH}}}-B(Z^1)(Z^2)$$

where

P is H or an amino-group-protecting moiety;

$X^2$ is selected from the group consisting of $$-\underset{O}{\overset{\|}{C}}-NH-, \quad -CH_2-NH-, \quad -\underset{OH}{\overset{|}{CH}}-CH_2-,$$

$$-\underset{OH}{\overset{|}{CH}}-\underset{OH}{\overset{|}{CH}}-, \quad -\underset{OH}{\overset{|}{CH}}-CH_2-NH-,$$

$$-CH=CH-, \quad -\underset{\overset{\|}{O}}{\overset{}{\underset{|}{C}}}-CH_2-,$$

$$-\underset{\overset{\|}{O}}{\overset{\overset{O}{\|}}{S}}-NH-, \quad -\underset{\overset{\|}{O}}{\overset{\overset{O}{\|}}{S}}-CH_2-, \text{ and}$$

$$-\underset{OH}{\overset{|}{CH}}-CH_2-\underset{O}{\overset{\|}{C}}-NH-;$$

R is hydrogen or alkyl;

$R^2$ and $R^3$ are independently selected from the group consisting of hydrogen, alkyl, cycloalkyl, aryl, heterocycle and $-CH_2-R^5$,
where $R^5$ is aryl, aralkyl, alkaryl, cycloalkyl, heterocycle, or -chalcogen-alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

32. A method for inhibiting cell adhesion in an animal comprising administering to said animal a proteasome inhibitor of the structure:

$$P-\underset{R}{\overset{}{\underset{|}{N}}}-\left[\underset{R^1}{\overset{}{\underset{|}{B^1}}}-X^1\right]_A-\underset{R^2}{\overset{}{\underset{|}{CH}}}-X^2-\underset{R^3}{\overset{}{\underset{|}{CH}}}-B(Z^1)(Z^2)$$

where

P is H or an amino-group-protecting moiety;

$X^2$ is selected from the group consisting of $$-\underset{O}{\overset{\|}{C}}-NH-, \quad -CH_2-NH-, \quad -\underset{OH}{\overset{|}{CH}}-CH_2-,$$

$$-\underset{OH}{\overset{|}{CH}}-\underset{OH}{\overset{|}{CH}}-, \quad -\underset{OH}{\overset{|}{CH}}-CH_2-NH-,$$

$$-CH=CH-, \quad -\underset{\overset{\|}{O}}{\overset{}{\underset{|}{C}}}-CH_2-,$$

$$-\underset{\overset{\|}{O}}{\overset{\overset{O}{\|}}{S}}-NH-, \quad -\underset{\overset{\|}{O}}{\overset{\overset{O}{\|}}{S}}-CH_2-, \text{ and}$$

$$-\underset{OH}{\overset{|}{CH}}-CH_2-\underset{O}{\overset{\|}{C}}-NH-;$$

R is hydrogen or alkyl;

$R^2$ and $R^3$ are independently selected from the group consisting of hydrogen, alkyl, cycloalkyl, aryl, heterocycle and $-CH_2-R^5$,
where $R^5$ is aryl, aralkyl, alkaryl, cycloalkyl, heterocycle, or -chalcogen-alkyl;

$Z^1$ and $Z^2$ are independently alkyl, hydroxy, alkoxy, aryloxy, or together form a dihydroxy compound having at least two hydroxy groups separated by at least two connecting atoms in a chain or ring, said chain or ring comprising carbon atoms, and optionally, a heteroatom or heteroatoms which can be N, S, or O; and A is 0.

33. A method for treating cancer in a patient, comprising administering to said patient a compound of claim 1.

34. A method for treating cancer in a patient, comprising administering to said patient a compound of claim 13.

35. A method for inhibiting HIV infection in an animal comprising administering to said animal a compound of claim 1.

36. A method for inhibiting HIV infection in an animal comprising administering to said animal a compound of claim 13.

37. A method for reducing the rate of degradation of p53 protein in a cell comprising administering to said cell a compound of claim 1.

38. A method for reducing the rate of degradation of p53 protein in a cell comprising administering to said cell a compound of claim 13.

39. A method for inhibiting cyclin degradation in a cell comprising contacting said cell with a compound of claim 1.

40. A method for inhibiting cyclin degradation in a cell comprising contacting said cell with a compound of claim 13.

41. A method for inhibiting NF-κB dependent cell adhesion in an animal comprising administering to said animal a compound of claim 1.

42. A method for inhibiting NF-κB dependent cell adhesion in an animal comprising administering to said animal a compound of claim 13.

* * * * *

UNITED STATES PATENT AND TRADEMARK OFFICE
CERTIFICATE OF CORRECTION

PATENT NO.  : 6,083,903
DATED       : July 4, 2000
INVENTOR(S) : Julian Adams, Yu-Ting Ma, Ross Stein, Matthew Baevsky, Louis Grenier and Louis Plamondon It is certified that error appears in the above-identified patent and that said Letters Patent is hereby corrected as shown below:

<u>Column 61,</u>
Line 39, "cycle and —$CH_2$—$R^5$, heterocycle, or —chalcogen-alkyl;" should be
-- cycle and —$CH_2$—$R^5$, where $R^5$ is aryl, aralkyl, alkaryl, cycloalkyl, heterocycle, or —chalcogen-alkyl; --.

<u>Column 63,</u>
Line 12, "The method of claim 26, wherein $R^2$, or $R^3$ is" should be -- The method of claim 19, wherein $R^2$, or $R^3$ is --.

Signed and Sealed this

Fifteenth Day of October, 2002

*Attest:*

*Attesting Officer*

JAMES E. ROGAN
*Director of the United States Patent and Trademark Office*